(12) United States Patent
Nowinski et al.

(10) Patent No.: US 9,731,010 B2
(45) Date of Patent: Aug. 15, 2017

(54) METHODS AND COMPOSITIONS FOR ENHANCED IMMUNOLOGICAL THERAPY AND TARGETING OF GRAM-POSITIVE BACTERIA

(71) Applicants: Robert C. Nowinski, New York, NY (US); Vincent A. Fischetti, New York, NY (US); Assaf Raz, New York, NY (US)

(72) Inventors: Robert C. Nowinski, New York, NY (US); Vincent A. Fischetti, New York, NY (US); Assaf Raz, New York, NY (US)

(73) Assignees: The Rockefeller University, New York, NY (US); Contrafect Corporation, Yonkers, NY (US)

( * ) Notice: Subject to any disclaimer, the term of this patent is extended or adjusted under 35 U.S.C. 154(b) by 0 days.

(21) Appl. No.: 14/641,571

(22) Filed: Mar. 9, 2015

(65) Prior Publication Data
US 2015/0306218 A1    Oct. 29, 2015

Related U.S. Application Data

(63) Continuation of application No. 13/520,601, filed as application No. PCT/US2011/000014 on Jan. 5, 2011, now Pat. No. 9,005,579.

(60) Provisional application No. 61/335,305, filed on Jan. 5, 2010.

(51) Int. Cl.
| | |
|---|---|
| *A61K 39/02* | (2006.01) |
| *A61K 39/04* | (2006.01) |
| *A61K 39/08* | (2006.01) |
| *A61K 39/40* | (2006.01) |
| *A61K 31/43* | (2006.01) |
| *C07K 16/12* | (2006.01) |
| *C12N 9/52* | (2006.01) |
| *A61K 31/18* | (2006.01) |
| *A61K 31/407* | (2006.01) |
| *A61K 31/47* | (2006.01) |
| *A61K 31/545* | (2006.01) |
| *A61K 31/7008* | (2006.01) |
| *A61K 31/7048* | (2006.01) |
| *A61K 38/02* | (2006.01) |
| *G01N 33/569* | (2006.01) |
| *A61K 39/00* | (2006.01) |

(52) U.S. Cl.
CPC .............. *A61K 39/40* (2013.01); *A61K 31/18* (2013.01); *A61K 31/407* (2013.01); *A61K 31/43* (2013.01); *A61K 31/47* (2013.01); *A61K 31/545* (2013.01); *A61K 31/7008* (2013.01); *A61K 31/7048* (2013.01); *A61K 38/02* (2013.01); *C07K 16/1271* (2013.01); *C12N 9/52* (2013.01); *G01N 33/56938* (2013.01); *A61K 2039/505* (2013.01); *G01N 2500/02* (2013.01); *G01N 2500/10* (2013.01)

(58) Field of Classification Search
CPC ................................ A61K 31/43; A61K 39/40
USPC ..... 424/9.1, 9.2, 130.1, 164.1, 234.1, 237.1, 424/239.1, 243.1, 247.1, 248.1
See application file for complete search history.

(56) References Cited

U.S. PATENT DOCUMENTS

| | | | |
|---|---|---|---|
| 6,773,706 B2 | 8/2004 | Schneewind et al. | |
| 9,005,579 B2 * | 4/2015 | Nowinski .............. | A61K 31/43 424/130.1 |

FOREIGN PATENT DOCUMENTS

| | | |
|---|---|---|
| WO | WO9937799 | 7/1999 |
| WO | WO03046007 | 6/2003 |
| WO | WO2009023160 | 2/2009 |

OTHER PUBLICATIONS

Barnett, TC et al (2004) A novel sortase, SrtC2, from *Streptococcus pyogenes* anchors a surface protein containing a QVPTGV motif to the cell wall J Bacteriol 186(17):5865-5875.
Boman, HG (2003) Antibacterial peptides: basic facts and emerging concepts J Intern Med 254(3):197-215.
Brown, KL et al (2006) Cationic host defense (antimicrobial) peptides Curr Opin Immunol 18(1):24-30.
Burnie, J et al (2002) Identification of ABC transporters in vancomycin-resistant enterococcus faecium as potential targets for antibody therapy FEMS Immuno & Medical Microbiol 33(3):179-189.
Chesneau, O et al (2005) Molecular analysis of resistance to streptogramin A compounds conferred by the Vga proteins of Staphylococci antimicrob Agents Chemother 49(3):973-980.
(Continued)

*Primary Examiner* — Rodney P Swartz
(74) *Attorney, Agent, or Firm* — Klauber & Jackson LLC

(57) ABSTRACT

The present invention relates to methods and compositions for use in modulating, including inhibiting the growth and/or reducing the virulence of, gram-positive bacteria. The present invention provides methods and compositions for disrupting the cell wall and/or cell membrane in gram-positive bacteria such that cell wall or cell membrane target(s) are rendered exposed or accessible and sensitive to a modulation thereof. Methods for modulation of one or more gram-positive bacterial cell wall or cell membrane targets in a gram-positive bacteria are provided comprising disrupting the cell wall such that the cell wall or cell membrane target, which is particularly a sortase, is rendered exposed or accessible and sensitive to a modifying, modulating or binding agent, which is particularly an antibody or fragment thereof, wherein the cell wall or cell membrane target is inaccessible or relatively insensitive to the modifying, modulating or binding agent in the absence of cell wall disruption.

15 Claims, 10 Drawing Sheets

(56) References Cited

OTHER PUBLICATIONS

Comfort, D et al (2004) A comparative genome analysis identifies distinct sorting pathways in gram-positive bacteria Infect Imunol 72(5):2710-2732.

Cossart, P et al (2000) Sortase, a universal target for therapeutic agents against gram-positive bacteria? Proc Natl Acad Sci 97(10):5013-5015.

DeDent, AC et al (2007) Distribution of protein A on the surface of *Staphylococcus aureus* J Bact 180(12):4473-4484.

Demchick, P et al (1996) The permeability of the wall fabric of *Escherichia coli* and Bacillus subtilis J Bact 178 (3):768-773.

Fischetti, VA (2003) Novel method to control pathogenic bacteria on human mucous membranes Ann NY Acad Sci 987:207-214.

Gaspar, AH et al (2005) Bacillus anthracis sortase A (SrtA) anchors LPXTG motif-containing surface proteins to the cell wall envelope J Bacteriol 187(13):4646-4655.

Gianfaldoni, C et al (2009) Sortase A confers protection against *Streptococcus pneumoniae* in mice Infect Immun 77 (7):2957-2961.

Hancock, RE (1999) Host defence (cationic) peptides: what is their future clinical potential? Drugs 57(4):469-473.

Higgins, DL et al (2005) Telavancin, a multifunctional lipoglycopeptide, disrupts both cell wall synthesis and cell membrane integrity in methicillin-resistant *Staphylococcus aureus* Antimicrob Agents Chemother 49(3):1127-1134.

Janiszewska, J et al (2003) Low molecular mass peptide dendrimers that express antimicrobial properties Bioorg Med Chem Let 13(21):3711-3713.

Jonsson, IM et al (2002) On the role of *Staphylococcus aureus* sortase and sortase-catalyzed surface protein anchoring in murine septic arthritis J Infect Dis 185(10):1417-1424.

Jonsson, IM et al (2003) The role of *Staphylococcus aureus* sortase A and sortase B in murine arthritis Microbes Infect 5(9):775-780.

Jonsson, IM et al (2010) Inactivation of the Ecs ABC transporter of *Staphylococcus aureus* attenuates virulence by altering composition and function of bacterial wall PLoSOne 5(12):e14209 doi: 10.1371/journal.pone.0014209.

Jung, ME et al (2005) Synthesis of (2R,3S) 3-amino-4-mercapto-2-butanol, a threonine analogue for covalent inhibition of sortases Bioorg Med Chem Lett 15(22):5076-5079.

Kruger, RG et al (2004) Inhibition of the *Staphylococcus aureus* sortase transpeptidase SrtA by phosphinic peptidomimetics Bioorg Med Chem 12(13):3723-3729.

Lee, HS et al (2005) Cyclic peptides of the nocardamine class from a marine-derived bacterium of the genus Streptomyces J Nat Prod 68(4):623-625.

Malachowa, N et al (2011) Characterization of a *Staphylococcus aureus* surface virulence factor that promotes resistance to oxidative killing and infection endocarditis Infect Immun 79(1):342-352 Oct. 11, 2010 epub.

Marraffini, LA et al (2004) Anchoring of surface proteins to the cell wall of *Staphylococcus aureus*. A conserved arginine residue is required for efficient catalysis of sortase A J Biol Chem 279(36):37763-37770.

Marraffini, LA et al (2006) Sortases and the art of anchoring proteins to the envelopes of gram-positive bacteria Microbial Mol Bio Rev 70(1):192-221.

Mazmanian, SK et al (1999) *Staphylococcus aureus* sortase, an enzyme that anchors surface proteins to the cell wall Science 285(5428):760-763.

Mazmanian, SK et al (2000) *Staphylococcus aureus* sortase mutants defective in the display of surface proteins and in the pathogenesis of animal infections PNAS 97(10):5510-5515.

Mitchell, DJ et al (2000) Polyarginine enters cells more efficiently than other polycationic homopolymers J Peptide Res 56(5):318-325.

Navarre, WW et al (1999) Surface proteins of gram-positive bacteria and mechanisms of their targeting to the cell wall envelope Microbiol Mol Biol Rev 63(1):174-229.

Raz, A et al (2008) Sortase A localizes to distinct foci on the *Streptococcus pyogenes* membrane PNAS 105 (47):18549-18554.

Scherrer, R et al (1971) Molecular sieving by the Bacillus megaterium cell wall and protoplast J Bact 107(3):718-735.

Schneewind, O et al (1992) Sorting of protein A to the Staphylococcal cell wall Cell 70(2):267-281.

Scott, CJ et al (2002) Irreversible inhibition of the bacterial cysteine protease-transpeptidase sortase (SrtA) by substrate-derived affinity labels J Biochem 366(Pt 3):953-958.

Siegel, SA et al (1993) Antibiotics enhance binding by human lipid A-reactive monoclonal antibody HA-1A to smooth gram-negative bacteria Infect Immunol 61(2):512-519.

Tew, GN et al (2002) De novo design of biomimetic antimicrobial polymers PNAS 99(8):5110-5114.

Ton-That, H et al (1999) Purification and characterization of sortase, the transpeptidase that cleaves surface proteins of *Staphylococcus aureus* at the LPXTG motif PNAS 96(22):12424-12429.

Ton-That, H et al (1999) Anchor structure of *Staphylococcal* surface proteins. IV. Inhibitors of the cell wall sorting reaction J Biol Chem 274(34):24316-24320.

Ton-That, H et al (2004) Assembly of pili in Gram-positive bacteria Trends Microbiol 12(5):228-234.

Wang, Z et al (2004) APD: the Antimicrobial Peptide Database NAR 32(Database issue):D590-D592.

Zasloff, M (2002) Antimicrobial peptides of multicellular organisms Nature 415(6870):389-395.

Zong, Y et al (2004) Crystal structures of *Staphylococcus aureus* sortase A and its substrate complex J Biol Chem 279(30):31383-31389.

\* cited by examiner

FIGURE 6A tggcgaatgggacgcgccctgtagcggcgcattaagcgcggcgggtgtggtggttacgcgcagcgtgaccgctacacttgccagcgccctagcg
cccgctcctttcgctttcttcccttcctttctcgccacgttcgccggctttccccgtcaagctctaaatcgggggctccctttaggggttccgatttagtg
ctttacggcacctcgaccccaaaaaacttgattagggtgatggttcacgtagtgggccatcgccctgatagacggttttttcgcccttttgacgttgga
gtccacgttctttaatagtggactcttgttccaaactggaacaacactcaaccctatctcggtctattcttttgatttataagggattttgccgatttc
ggcctattggttaaaaaatgagctgatttaacaaaaatttaacgcgaattttaacaaaatattaacgtttacaatttcaggtggcacttttcgggg
aaatgtgcgcggaaccccctatttgttattttttctaaatacattcaaatatgtatccgctcatgagacaataaccctgataaatgcttcaataatatt
gaaaaaggaagagtatgagtattcaacatttccgtgtcgcccttattccctttttgcggcattttgccttcctgttttttgctcacccagaaacgctgg
tgaaagtaaaagatgctgaagatcagttgggtgcacgagtgggttacatcgaactggatctcaacagcggtaagatccttgagagttttcgcccc
gaagaacgttttccaatgatgagcacttttaaagttctgctatgtggcgcggtattatcccgtattgacgccgggcaagagcaactcggtcgccgc
atacactattctcagaatgacttggttgagtactcaccagtcacagaaaagcatcttacggatggcatgacagtaagagaattatgcagtgctgc
cataaccatgagtgataacactgcggccaacttacttctgacaacgatcggaggaccgaaggagctaaccgcttttttgcacaacatgggggat
catgtaactcgccttgatcgttgggaaccggagctgaatgaagccataccaaacgacgagcgtgacaccacgatgcctgcagcaatggcaaca
acgttgcgcaaactattaactggcgaactacttactctagcttcccggcaacaattaatagactggatggaggcggataaagttgcaggaccact
tctgcgctcggcccttccggctggctggtttattgctgataaatctggagccggtgagcgtgggtctcgcggtatcattgcagcactggggccaga
tggtaagccctcccgtatcgtagttatctacacgacggggagtcaggcaactatggatgaacgaaatagacagatcgctgagataggtgcctca
ctgattaagcattggtaactgtcagaccaagtttactcatatatactttagattgatttaaaacttcattttaatttaaaaggatctaggtgaagat
ccttttttgataatctcatgaccaaaatcccttaacgtgagttttcgttccactgagcgtcagaccccgtagaaaagatcaaaggatcttcttgagat
cctttttttctgcgcgtaatctgctgcttgcaaacaaaaaaaccaccgctaccagcggtggtttgtttgccggatcaagagctaccaactcttttcc
gaaggtaactggcttcagcagagcgcagataccaaatactgtccttctagtgtagccgtagttaggccaccacttcaagaactctgtagcaccgc
ctacatacctcgctctgctaatcctgttaccagtggctgctgccagtggcgataagtcgtgtcttaccgggttggactcaagacgatagttaccgg
ataaggcgcagcggtcgggctgaacggggggttcgtgcacacagcccagcttggagcgaacgacctacaccgaactgagatacctacagcgtg
agctatgagaaagcgccacgcttcccgaaggagaaaggcggacaggtatccggtaagcggcagggtcggaacaggagagcgcacgaggga
gcttccagggggaaacgcctggtatctttatagtcctgtcgggtttcgccacctctgacttgagcgtcgatttttgtgatgctcgtcagggggcgg
agcctatggaaaaacgccagcaacgcggcctttttacggttcctggccttttgctggccttttgctcacatgttctttcctgcgttatcccctgattct
gtggataaccgtattaccgcctttgagtgagctgataccgctcgccgcagccgaacgaccgagcgcagcgagtcagtgagcgaggaagcggaa
gagcgcctgatgcggtattttctccttacgcatctgtgcggtatttcacaccgcatatatggtgcactctcagtacaatctgctctgatgccgcatag
ttaagccagtatacactccgctatcgctacgtgactgggtcatggctgcgccccgacacccgccaacacccgctgacgcgccctgacgggcttgt
ctgctcccggcatccgcttacagacaagctgtgaccgtctccgggagctgcatgtgtcagaggttttcaccgtcatcaccgaaacgcgcgaggca
gctgcggtaaagctcatcagcgtggtcgtgaagcgattcacagatgtctgcctgttcatccgcgtccagctcgttgagtttctccagaagcgttaat
gtctggcttctgataaagcgggccatgttaagggcggttttttcctgtttggtcactgatgcctccgtgtaagggggatttctgttcatgggggtaat
gataccgatgaaacgagagaggatgctcacgatacgggttactgatgatgaacatgcccggttactggaacgttgtgagggtaaacaactggc
ggtatggatgcggcgggaccagagaaaaatcactcagggtcaatgccagcgcttcgttaatacagatgtaggtgttccacagggtagccagca
gcatcctgcgatgcagatccggaacataatggtgcagggcgctgacttccgcgtttccagactttacgaaacacggaaaccgaagaccattcat
gttgttgctcaggtcgcagacgttttgcagcagcagtcgcttcacgttcgctcgcgtatcggtgattcattctgctaaccagtaaggcaaccccgcc
agcctagccgggtcctcaacgacaggagcacgatcatgcgcacccgtggggccgccatgccggcgataatggcctgcttctcgccggaaacgttt
ggtggcgggaccagtgacgaaggcttgagcgagggcgtgcaagattccgaataccgcaagcgacaggccgatcatcgtcgcgctccagcgaa
agcggtcctcgccgaaaatgacccagagcgctgccggcacctgtcctacgagttgcatgataaagaagacagtcataagtgcggcgacgatag
tcatgccccgcgcccaccggaaggagctgac

FIGURE 6B tgggttgaaggctctcaagggcatcggtcgagatcccggtgcctaatgagtgagctaacttacattaattgcgttgcgctcactgcccgctttcca
gtcgggaaacctgtcgtgccagctgcattaatgaatcggccaacgcgcggggagaggcggtttgcgtattgggcgccagggtggttttctttca
ccagtgagacgggcaacagctgattgcccttcaccgcctggccctgagagagttgcagcaagcggtccacgctggtttgccccagcaggcgaaa
atcctgtttgatggtggttaacggcgggatataacatgagctgtcttcggtatcgtcgtatcccactaccgagatatccgcaccaacgcgcagccc
ggactcggtaatggcgcgcattgcgcccagcgccatctgatcgttggcaaccagcatcgcagtgggaacgatgccctcattcagcatttgcatgg
tttgttgaaaaccggacatggcactccagtcgccttcccgttccgctatcggctgaatttgattgcgagtgagatatttatgccagccagccagac
gcagacgcgccgagacagaacttaatgggcccgctaacagcgcgatttgctggtgacccaatgcgaccagatgctccacgcccagtcgcgtacc
gtcttcatgggagaaaataatactgttgatgggtgtctggtcagagacatcaagaaataacgccggaacattagtgcaggcagcttccacagca
atggcatcctggtcatccagcggatagttaatgatcagcccactgacgcgttgcgcgagaagattgtgcaccgccgctttacaggcttcgacgcc
gcttcgttctaccatcgacaccaccacgctggcacccagttgatcggcgcgagatttaatcgccgcgacaatttgcgacggcgcgtgcagggcca
gactggaggtggcaacgccaatcagcaacgactgtttgcccgccagttgttgtgccacgcggttgggaatgtaattcagctccgccatcgccgctt
ccacttttccgcgttttcgcagaaacgtggctggcctggttcaccacgcgggaaacggtctgataagagacaccggcatactctgcgacatcgt
ataacgttactggtttcacattcaccaccctgaattgactctcttccgggcgctatcatgccataccgcgaaaggttttgcgccattcgatggtgtcc
gggatctcgacgctctcccttatgcgactcctgcattaggaagcagcccagtagtaggttgaggccgttgagcaccgccgccgcaaggaatggtg
catgcaaggagatggcgcccaacagtcccccggccacggggcctgccaccatacccacgccgaaacaagcgctcatgagcccgaagtggcga
gcccgatcttccccatcggtgatgtcggcgatataggcgccagcaaccgcacctgtggcgccggtgatgccggccacgatgcgtccggcgtaga
ggatcgagatctcgatcccgcgaaattaatacgactcactataggggaattgtgagcggataacaattcccctctagaaataattttgtttaactt
taagaaggagatatacatatggctagcatgactggtggacagcaaatgggtcgcggatccaatgtgcagggacatcttcccctcgtaccacgag
gttcaaagcttcatcatcatcatcatcatctgaagttctgttccaggggcccgtcgacaaaccacatatcgataattatcttcacgataaagata
aagatgaaaagattgaacaatatgataaaaatgtaaaagaacaggcgagtaaagataaaaagcagcaagctaaaccctcaaattccgaaaga
taaatcgaaagtggcaggctatattgaaattccagatgctgatattaaagaaccagtatatccaggaccagcaacacctgaacaattaaataga
ggtgtaagctttgcagaagaaaacgaatcactagatgatcaaaatatttcaattgcaggacacactttcattgaccgtccgaactatcaatttac
aaatcttaaagcagccaaaaaaggtagtatggtgtactttaaagttggtaatgaaacacgtaagtataaaatgacaagtataagagatgttaag
cctacagatgtagaagttctagatgaacaaaaaggtaaagataaacaattaacattaattacttgtgatgattacaatgaaaagacaggcgttt
gggaaaaacgtaaaatctttgtagctacagaagtcaaataagcggccgcactcgagcaccaccaccaccactgagatccggctgctaaca
aagcccgaaaggaagctgagttggctgctgccaccgctgagcaataactagcataacccttggggcctctaaacgggtcttgaggggttttttg
ctgaaaggaggaactatatccggat

SEQUENCE LISTING

```
<160> NUMBER OF SEQ ID NOS: 7

<210> SEQ ID NO 1
<211> LENGTH: 37
<212> TYPE: DNA
<213> ORGANISM: Staphylococcus aureus

<400> SEQUENCE: 1
cccgtcgaca aaccacatat cgataattat cttcacg                              37

<210> SEQ ID NO 2
<211> LENGTH: 43
<212> TYPE: DNA
<213> ORGANISM: Staphylococcus aureus
```

```
<400> SEQUENCE: 2
ggggcggccg cttatttgac ttctgtagct acaaagattt tac                        43

<210> SEQ ID NO 3
<211> LENGTH: 226
<212> TYPE: PRT
<213> ORGANISM: Staphylococcus aureus

<400> SEQUENCE: 3

Met Ala Ser Met Thr Gly Gly Gln Gln Met Gly Arg Gly Ser Asn Val
 1               5                  10                  15

Gln Gly His Leu Pro Leu Val Pro Arg Gly Ser Lys Leu His His His
            20                  25                  30

His His His Leu Glu Val Leu Phe Gln Gly Pro Val Asp Lys Pro His
        35                  40                  45

Ile Asp Asn Tyr Leu His Asp Lys Asp Lys Asp Glu Lys Ile Glu Gln
 50                  55                  60

Tyr Asp Lys Asn Val Lys Glu Gln Ala Ser Lys Asp Lys Lys Gln Gln
 65                  70                  75                  80

Ala Lys Pro Gln Ile Pro Lys Asp Lys Ser Lys Val Ala Gly Tyr Ile
                85                  90                  95

Glu Ile Pro Asp Ala Asp Ile Lys Glu Pro Val Tyr Pro Gly Pro Ala
            100                 105                 110

Thr Pro Glu Gln Leu Asn Arg Gly Val Ser Phe Ala Glu Glu Asn Glu
        115                 120                 125

Ser Leu Asp Asp Gln Asn Ile Ser Ile Ala Gly His Thr Phe Ile Asp
130                 135                 140

Arg Pro Asn Tyr Gln Phe Thr Asn Leu Lys Ala Ala Lys Lys Gly Ser
145                 150                 155                 160

Met Val Tyr Phe Lys Val Gly Asn Glu Thr Arg Lys Tyr Lys Met Thr
                165                 170                 175

Ser Ile Arg Asp Val Lys Pro Thr Asp Val Glu Val Leu Asp Glu Gln
            180                 185                 190

Lys Gly Lys Asp Lys Gln Leu Thr Leu Ile Thr Cys Asp Asp Tyr Asn
        195                 200                 205

Glu Lys Thr Gly Val Trp Glu Lys Arg Lys Ile Phe Val Ala Thr Glu
    210                 215                 220

Val Lys
225

<210> SEQ ID NO 4
<211> LENGTH: 5
<212> TYPE: PRT
<213> ORGANISM: Artificial Sequence
<220> FEATURE:
<223> OTHER INFORMATION: sorting motif
<221> NAME/KEY: VARIANT
<222> LOCATION: (3)...(3)
<223> OTHER INFORMATION: Xaa can be any amino acid

<400> SEQUENCE: 4

Leu Pro Xaa Thr Gly
 1               5

<210> SEQ ID NO 5
<211> LENGTH: 6
<212> TYPE: PRT
<213> ORGANISM: Artificial Sequence
```

```
<220> FEATURE:
<223> OTHER INFORMATION: sorting motif

<400> SEQUENCE: 5

Gln Val Pro Thr Gly Val
 1               5

<210> SEQ ID NO 6
<211> LENGTH: 5
<212> TYPE: PRT
<213> ORGANISM: Artificial Sequence
<220> FEATURE:
<223> OTHER INFORMATION: srtA substrate peptide

<400> SEQUENCE: 6

Leu Pro Glu Thr Gly
 1               5

<210> SEQ ID NO 7
<211> LENGTH: 6057
<212> TYPE: DNA
<213> ORGANISM: Unknown
<220> FEATURE:
<223> OTHER INFORMATION: vector pAR203

<400> SEQUENCE: 7
```

| | | | | | |
|---|---|---|---|---|---|
| tggcgaatgg | gacgcgccct | gtagcggcgc | attaagcgcg | gcgggtgtgg | tggttacgcg | 60 |
| cagcgtgacc | gctacacttg | ccagcgccct | agcgcccgct | cctttcgctt | tcttcccttc | 120 |
| ctttctcgcc | acgttcgccg | gctttccccg | tcaagctcta | aatcgggggc | tccctttagg | 180 |
| gttccgattt | agtgctttac | ggcacctcga | ccccaaaaaa | cttgattagg | gtgatggttc | 240 |
| acgtagtggg | ccatcgccct | gatagacggt | ttttcgccct | tgacgttgg | agtccacgtt | 300 |
| ctttaatagt | ggactcttgt | tccaaactgg | aacaacactc | aaccctatct | cggtctattc | 360 |
| ttttgattta | taagggattt | tgccgatttc | ggcctattgg | ttaaaaaatg | agctgattta | 420 |
| acaaaaattt | aacgcgaatt | ttaacaaaat | attaacgttt | acaatttcag | gtggcacttt | 480 |
| tcggggaaat | gtgcgcggaa | cccctatttg | tttatttttc | taaatacatt | caaatatgta | 540 |
| tccgctcatg | agacaataac | cctgataaat | gcttcaataa | tattgaaaaa | ggaagagtat | 600 |
| gagtattcaa | catttccgtg | tcgcccttat | tccctttttt | gcggcatttt | gccttcctgt | 660 |
| ttttgctcac | ccagaaacgc | tggtgaaagt | aaaagatgct | gaagatcagt | tgggtgcacg | 720 |
| agtgggttac | atcgaactgg | atctcaacag | cggtaagatc | cttgagagtt | ttcgccccga | 780 |
| agaacgtttt | ccaatgatga | gcacttttaa | agttctgcta | tgtggcgcgg | tattatcccg | 840 |
| tattgacgcc | gggcaagagc | aactcggtcg | ccgcatacac | tattctcaga | atgacttggt | 900 |
| tgagtactca | ccagtcacag | aaaagcatct | tacggatggc | atgacagtaa | gagaattatg | 960 |
| cagtgctgcc | ataaccatga | gtgataacac | tgcggccaac | ttacttctga | caacgatcgg | 1020 |
| aggaccgaag | gagctaaccg | cttttttgca | caacatgggg | gatcatgtaa | ctcgccttga | 1080 |
| tcgttgggaa | ccggagctga | atgaagccat | accaaacgac | gagcgtgaca | ccacgatgcc | 1140 |
| tgcagcaatg | gcaacaacgt | tgcgcaaact | attaactggc | gaactactta | ctctagcttc | 1200 |
| ccggcaacaa | ttaatagact | ggatggaggc | ggataaagtt | gcaggaccac | ttctgcgctc | 1260 |
| ggcccttccg | gctggctggt | ttattgctga | taaatctgga | gccggtgagc | gtgggtctcg | 1320 |
| cggtatcatt | gcagcactgg | ggccagatgg | taagccctcc | cgtatcgtag | ttatctacac | 1380 |
| gacggggagt | caggcaacta | tggatgaacg | aaatagacag | atcgctgaga | taggtgcctc | 1440 |

```
actgattaag cattggtaac tgtcagacca agtttactca tatatacttt agattgattt    1500
aaaacttcat ttttaattta aaaggatcta ggtgaagatc cttttttgata atctcatgac   1560 caaaatccct taacgtgagt tttcgttcca ctgagcgtca gaccccgtag aaaagatcaa    1620
aggatcttct tgagatcctt tttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag cgcagcggt cgggctgaac ggggggttcg tgcacacagc ccagcttgga    1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggcctttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaagggggg atttctgttc atgggggtaa   2880
tgataccgat gaaacgagag aggatgctca cgatacgggt tactgatgat gaacatgccc   2940
ggttactgga acgttgtgag ggtaaacaac tggcggtatg gatgcggcgg gaccagagaa   3000
aaatcactca gggtcaatgc cagcgcttcg ttaatacaga tgtaggtgtt ccacagggta   3060
gccagcagca tcctgcgatg cagatccgga acataatggt gcagggcgct gacttccgcg   3120
tttccagact ttacgaaaca cggaaaccga agaccattca tgttgttgct caggtcgcag   3180
acgttttgca gcagcagtcg cttcacgttc gctcgcgtat cggtgattca ttctgctaac   3240
cagtaaggca accccgccag cctagccggg tcctcaacga caggagcacg atcatgcgca   3300
cccgtggggc cgccatgccg cgataatgg cctgcttctc gccgaaacgt tggtggcgg    3360 gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgccccgcgc ccaccggaag gagctgactg ggttgaaggc tctcaagggc atcggtcgag   3600
atcccggtgc ctaatgagtg agctaactta cattaattgc gttgcgctca ctgcccgctt   3660
tccagtcggg aaacctgtcg tgccagctgc attaatgaat cggccaacgc gcggggagag   3720
gcggtttgcg tattgggcgc cagggtggtt tttcttttca ccagtgagac gggcaacagc   3780
tgattgccct tcaccgcctg gccctgagag agttgcagca agcggtccac gctggtttgc   3840
```

```
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggttttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga ataacgccg gaacattagt gcaggcagct     4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg gcaacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg gcgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccataccc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact ataggggaat tgtgagcgga taacaattcc    5160
cctctagaaa taattttgtt taactttaag aaggagatat acatatggct agcatgactg    5220
gtggacagca aatgggtcgc ggatccaatg tgcaggaca tcttcccctc gtaccacgag     5280
gttcaaagct tcatcatcat catcatcatc tggaagttct gttccagggg cccgtcgaca    5340
aaccacatat cgataattat cttcacgata aagataaaga tgaaaagatt gaacaatatg    5400
ataaaaatgt aaaagaacag gcgagtaaag ataaaaagca gcaagctaaa cctcaaattc    5460
cgaaagataa atcgaaagtg gcaggctata ttgaaattcc agatgctgat attaaagaac    5520
cagtatatcc aggaccagca acacctgaac aattaaatag aggtgtaagc tttgcagaag    5580
aaaacgaatc actagatgat caaaatattt caattgcagg acacactttc attgaccgtc    5640
cgaactatca atttacaaat cttaaagcag ccaaaaaagg tagtatggtg tactttaaag    5700
ttggtaatga aacacgtaag tataaaatga caagtataag agatgttaag cctcagatg    5760 tagaagttct agatgaacaa aaaggtaaag ataaacaatt aacattaatt acttgtgatg    5820
attacaatga aagacaggc gtttgggaaa acgtaaaat ctttgtagct acagaagtca     5880
aataagcggc cgcactcgag caccaccacc accaccactg agatccggct gctaacaaag    5940
cccgaaagga agctgagttg gctgctgcca ccgctgagca ataactagca taaccccttg    6000
gggcctctaa acgggtcttg aggggttttt tgctgaaagg aggaactata tccggat      6057
```

METHODS AND COMPOSITIONS FOR ENHANCED IMMUNOLOGICAL THERAPY AND TARGETING OF GRAM-POSITIVE BACTERIA

CROSS REFERENCE TO RELATED APPLICATIONS

The present application is a Continuation of National Stage Application Ser. No. 13/520,601, filed Oct. 25, 2012, now U.S. Pat. No. 9,005,579, which claims priority from PCT Application No. PCT/US2011/000014 filed on Jan. 5, 2011, which claims priority from U.S. Provisional Application Ser. No. 61/335,305 filed Jan. 5, 2010. Applicants claim the benefits of 35 U.S.C. §120 as to the said PCT Application and priority under §119 as to the said Provisional application, and the entire disclosures of both applications are incorporated herein by reference in their entireties.

FIELD OF THE INVENTION

The present invention relates to methods and compositions for use in modulating, including inhibiting the growth and/or reducing the virulence of, gram-positive bacteria. The present invention relates generally to disrupting the cell wall and/or cell membrane in gram-positive bacteria such that cell wall or cell membrane target(s) are rendered more exposed or more accessible and sensitive to a modulation thereof.

BACKGROUND OF THE INVENTION

Gram-positive bacteria are surrounded by a cell wall containing polypeptides and polysaccharide. The gram-positive cell wall appears as a broad, dense wall that is 20-80 nm thick and consists of numerous interconnecting layers of peptidoglycan. Between 60% and 90% of the gram-positive cell wall is peptidoglycan, providing cell shape, a rigid structure, and resistance to osmotic shock. The cell wall does not exclude the Gram stain crystal violet, allowing cells to be stained purple, and therefore "Gram-positive." The peptidoglycan molecule's backbone is comprised of glucose derivatives N-acetylglucosamine (NAG) and N-acetylmuramic acid (NAM), interconnected by peptides. Interwoven in the peptidoglycan cell wall are teichoic acids and lipoteichoic acids. The gram-positive peptidoglycan is studded with surface proteins, including enzymes, invasins, adhesins and other binding proteins.

Gram-positive bacteria include but are not limited to the genera *Actinomyces, Bacillus, Listeria, Lactococcus, Staphylococcus, Streptococcus, Enterococcus, Mycobacterium, Corynebacterium,* and *Clostridium.* Medically relevant species include *Streptococcus pyogenes, Streptococcus pneumoniae, Staphylococcus aureus,* and *Enterococcus faecalis. Bacillus* species, which are spore-forming, cause anthrax and gastroenteritis. Spore-forming *Clostridium* species are responsible for botulism, tetanus, gas gangrene and pseudomembranous colitis. *Corynebacterium* species cause diphtheria, and *Listeria* species cause meningitis.

The cell walls of gram-negative bacteria are more chemically complex, thinner and less compact. In gram-negative bacteria, peptidoglycan makes up 5-20% of the cell wall and is not the outermost layer, lying between the plasma membrane and an outer membrane. The outer membrane is composed of lipopolysaccharide (LPS) which is an endotoxin. The LPS prevents penetration of gram stain, rendering these bacteria "gram negative." Gram-negative and Gram-positive bacteria can be susceptible to distinct antibacterial agents and therapeutic molecules.

Antibacterials that inhibit cell wall synthesis, such as penicillins and cephalosporins, interfere with the linking of the interpeptides of peptidoglycan and weaken the cell wall of both gram positive and gram negative bacteria. Because the peptidoglycans of gram-positive bacteria are exposed, gram-positive bacteria are more susceptible to these antibiotics. Advantageously, eukaryotic cells lack cell walls and are not susceptible to these drugs or other cell wall agents.

Thus, in gram-positive bacteria, the cell membrane is surrounded by a cell wall containing polypeptides and polysaccharide that is 20-80 nm thick and consists of numerous interconnecting layers of peptidoglycan. The cell membrane carries out multiple functions and contains enzymes of biosynthetic pathways for synthesis of cell wall phospholipids, peptidoglycans, etc. The cell membrane also contains carrier proteins, transport proteins, and permeases for transport of organics and inorganics across the cell membrane. Components for control of chemotaxis are located in the cell membrane. Gram positive cell membrane protein families include penicillin binding proteins, ABC transporters, and potassium channels.

Gram-positive surface proteins are attached to the cell wall and displayed on the surface via a mechanism involving the enzyme(s) sortase. The genomes of most gram-positive bacteria encode two or more sortase enzymes, which have different sorting motif target sequences. The most common sorting target sequence is an LPXTG (SEQ ID NO: 4) motif. The sorting mechanism was first characterized in *S. aureus*, where the srtA (surface protein sorting A) gene was identified as restoring the defect in cell wall anchoring of Protein A (Mazmanian, S. K. et al (1999) Science 285:760-763; Ton-That, H. et al (1999) PNAS 96(22):12424-12429). Protein A is an *S. aureus* surface protein and is synthesized as a precursor with an N-terminal signal peptide and a C-terminal sorting signal, an LPXTG (SEQ ID NO: 4) motif (Schneewind, O. et al (1992) Cell 70:267-281). The Protein A sorting signal directs the peptide to the cell wall envelope and it is then cleaved between the threonine and the glycine of the LPXTG (SEQ ID NO: 4) sequence. The *S. aureus* sortase B anchors iron-regulated surface determinant C (IsdC), which has an NPQTN motif sorting signal (Marraffini, L. A. et al (2004) J Biol Chem 279:37763-37770). *Streptococcal* SrtC2 recognizes surface proteins with QVPTGV (SEQ ID NO: 5) motif signals (Barnett, T. C. et al (2004) J Bact 186:5865-5875).

The *S. aureus* sortase SrtA is a cell membrane-anchored enzyme and has been demonstrated to be absolutely required for the anchoring of *S. aureus* surface proteins to the cell wall envelope and essential for pathogenesis of animal infections (Mazmanian, S. K. et al (2000) PNAS 97(10): 5510-5515; Cossart, P and Jonquieres, R. (2000) PNAS 97(10):5013-5015). In these studies, the functional assembly of all *staphylococcal* adhesins, protein A, fibronectin-binding proteins (FnbA and FnbB) and clumping factors (ClfA and ClfB) was abolished in sortase SrtA mutants. Sortase SrtA cleaves surface protein precursors between the threonine and the glycine of the LPXTG (SEQ ID NO: 4) motif and then captures the C-terminal carboxyl by formation of a thioester bind with its active sulfhydryl. The sortase then completes the transpeptidation reaction via nucleophilic attack of the amino group of the lipid II peptidoglycan precursor, forming an amide bond between the surface peptide and cell wall cross bridge and regenerating its active site sulfhydryl (Ton-That, H and Schneewind, O. (1999) J. Biol Chem 274:24316-24320)

Scientific studies point to sortase and sortase family members as playing a universal role in gram-positive bacteria. Surface proteins with C-terminal LPXTG (SEQ ID NO: 4) motifs have been found in all pathogenic gram-positive bacteria (Navarre, W. W. et al (1999) Microbiol Mol Biol Rev 63:174-229). Sortase homologs have been identified in each of and various *Bacillus, Enterococcus, Actinomyces, Lactococcus, Listeria, Clostridium* and *Corynebacterium* (Mazmanian, S. K. et al (1999) Science 285:760-763; Navarre, W. W. and Schneewind, O. (1999) Microbiol Mol Biol Rev 63:174-229). In murine models of organ abscesses, infectious arthritis, and endocarditis, *Staphylococcal* sortase srtA mutants display significant defects in pathogenesis (Jonsson, I. M. et al (2002) J Infect Dis 185:1417-1424; Jonsson, I. M. et al (2003) Microb Infect 5:775-780).

Fractionation and Western blotting experiments using recombinant sortase antibodies have shown that sortase is a bacterial membrane associated protein (Mazmanian, S. K. et al (2000) RNAS 97(10):5510-5515). For these experiments, *S. aureus* cultures were fractionated into extra cellular medium, cell wall digest, cytosol, and membrane compartments, and sortase was found only in the membrane. Immunoblotting with sortase-specific antibodies shows that the sortase is not removed by treatment of *Staphylococci* with trypsin (De Dent, A. C. et al (2007) J Bact 189(12):4473-4484). While the particular distribution of many surface proteins, including proteins in the bacterial membrane, has been determined, the actual or precise distribution of sortase A in the membrane is not readily determinable, including in *S. aureus* for instance.

Under ordinary growth and standard culture conditions, proteases and antibodies have limited accessibility to sortase on the bacterial surface (De Dent A. C. et al (2007) J Bact 189(12):4473-4484). Recent studies have confirmed its location at the cell membrane using fixed cells (Raz A and Fischetti V A (2008) PNAS 105(47):18549-18554).

It is apparent that antibody(ies) or other large molecules and macromolecules (for example protease) cannot readily access their cell membrane targets without crossing the cell wall and peptidoglycan layer. Thus, for instance, the cell membrane protein sortase is not ideally susceptible as a target for directed therapy, including antibody therapy. Thus, cell membrane embedded and/or associated proteins, or other proteins below or within the gram positive bacterial cell wall, are not readily accessible and ideally susceptible to certain therapeutic intervention due to the cell wall and the thick peptidoglycan. Therefore, in view of the limited accessibility of gram-positive cell membrane proteins, such as sortase, it should be apparent that there still exists a need in the art for methods, approaches and therapeutic compositions to permit effective targeting and modulation of bacterial cell membrane proteins, such as sortase, including by antibodies or other enzymes or macromolecules.

The citation of references herein shall not be construed as an admission that such is prior art to the present invention.

SUMMARY OF THE INVENTION

In accordance with the present invention, methods and compositions are provided for enhancing therapy and targeting of cell wall and/or cell membrane targets in gram positive bacteria. In a particular aspect of the invention, these targets are ordinarily embedded in the cell wall or associated with or embedded in the cell membrane and rendered less accessible or poorly sensitive to agents or macromolecules, such as antibodies. As noted above, in the case of *S. aureus*, it has been demonstrated that sortase, an attractive target for therapeutic intervention in treatment and prophylaxis of bacterial infection, is not ideally accessible to either protease or antibody to the cell-membrane associated protein target. Similarly, targeting of other cell membrane proteins would benefit from a means to direct and facilitate access to the membrane proteins through the cell wall and peptidoglycan.

By combining low doses of antibiotics, at levels which do not significantly affect bacterial cell growth, with antibody, including antibody directed against the cell membrane protein sortase, the antibody is able to access or target the cell membrane protein (e.g., sortase) at levels sufficient to be visualized by immunofluorescence, and enhanced effects limiting or reducing bacterial cell growth are observed. Thus, combinations of antibiotic at sub-MIC doses with agent(s) directed against bacterial cell membrane protein(s) provide enhanced reduction of bacterial cell growth and targeting of the agent(s) to the cell membrane protein(s). The present method provides enhanced targeting of an agent to the cell membrane, or across the cell wall, by altering the cell wall or growth of the bacteria such that the cell wall is compromised, and the agent can thereby effectively and sufficiently target the cell membrane or cross the cell wall and peptidoglycan to access its appropriate target. The effect of the combination(s) of the invention are distinct from a synergistic killing or growth reduction of traditional antibiotic(s) and anti-bacterial agent(s) combinations. In the present instance and in accordance with the invention, the cell wall disrupting agent (for instance antibiotic) serves to enhance delivery of the agent(s) to its target across the cell wall and peptidoglycan. The cell wall disrupting agent (for instance antibiotic) thereby serves as a targeting or delivery agent in the methods and uses provided herein.

The invention provides a method for modulation of one or more gram-positive bacterial cell targets in a gram-positive bacteria comprising disrupting the cell wall and/or peptidoglycan such that the target, particularly located within or beneath the cell wall, including in the cell membrane, associated with the cell membrane, or in the periplasmic space, is rendered exposed or more accessible and sensitive to a modifying, modulating or binding agent, wherein the target is inaccessible or relatively insensitive to the modifying, modulating or binding agent in the absence of cell wall disruption. In a further aspect the invention provides a method for modulation of one or more gram-positive bacterial cell targets in a gram-positive bacteria comprising disrupting the cell wall and/or peptidoglycan such that the target, particularly located within or beneath the cell wall, including in the cell membrane, associated with the cell membrane, or in the periplasmic space, is rendered more exposed or more accessible and more sensitive to a modifying, modulating or binding agent, wherein the target is less accessible or less sensitive to the modifying, modulating or binding agent in the absence of cell wall disruption. Thus, the invention provides a method for modification or modulation of one or more gram-positive bacterial cell wall or cell membrane targets in a gram-positive bacteria comprising disrupting the cell wall such that the cell wall or cell membrane target is rendered exposed or accessible and sensitive to a modifying, modulating or binding agent, wherein the cell wall or cell membrane target is inaccessible or relatively insensitive to the modifying, modulating or binding agent in the absence of cell wall disruption. Gram positive bacteria are known and can readily be identified and may be selected from *Actinomyces, Bacillus, Listeria, Lactococcus, Staphylococcus, Streptococcus, Enterococcus, Mycobacterium, Corynebacterium,* and *Clostridium*. In a particular aspect the target bacteria is a clinically or medically significant genus or strain.

In an aspect of the invention, the modifying, modulating or binding agent is selected from an antibody or fragment thereof. An antibody may include a full antibody molecule or a fragment or portion thereof, including single domain antibodies or camelid antibodies, and engineered, recombinant, humanized or chimeric antibodies. Bispecific antibodies or antibodies fused or linked to antibacterial agents, toxins, cationic peptides, antimicrobial peptides, cell wall degrading enzymes or such other functional, targeting, or cell wall disrupting entities or molecules are also contemplated.

In an aspect of the invention, the cell wall or cell membrane target is a sortase or a sortase-like family member.

In a further aspect of the invention, the modifying, modulating or binding agent is a ligand, a bioactive peptide, or an enzyme. In a further aspect of the invention, the cell wall or cell membrane target is penicillin binding protein, an ABC transporter, a channel protein, a pore protein or pore component, β-lactamase, or other bacterial proteins that either influence or are required for growth, virulence or resistance to antibiotic treatment. In an aspect of the invention, the cell wall or cell membrane target is a sortase, penicillin binding protein, ABC transporter, channel protein, surface factor, or other bacterial cell wall or cell membrane protein that influences or is required for growth, virulence or resistance to antibiotic(s). In an aspect of the invention, the cell wall or cell membrane target is a sortase, penicillin binding protein, ABC transporter, channel protein, surface factor, or other bacterial cell membrane protein that influences or is required for growth, virulence or resistance to antibiotic(s). In an aspect of the invention, the cell wall or cell membrane target is selected from a sortase, a penicillin binding protein, an ABC transporter, a potassium channel protein and a surface factor promoting resistance to oxidative killing. In an aspect of the invention, the cell wall or cell membrane target is further selected from Table 1.

In an embodiment of the invention, disrupting the cell wall is accomplished using one or more antibiotics. The cell wall disrupting agents may have inherent antibacterial activity, and may be utilized at a concentration which is less than the minimally inhibitory concentration (MIC) of said agent, or at a concentration which is at or above the MIC of said agent. The cell wall disrupting agent may be an antibiotic. The cell wall disrupting agent may be an antibiotic that directly affects cell wall peptidoglycan biosynthesis or may indirectly affect the cell wall permeability by altering DNA or protein synthesis and/or cell growth or division. The antibiotic may be selected from a glycopeptides, penicillin or polypeptide. The antibiotic may be selected from vancomycin, teichoplanin, oxacillin, ampicillin, penicillin, cloaxacillin and bacitracin. The antibiotic may be a quinolone, macrolide or sulfonamide. The cell wall disrupting agent may an antibiotic selected from a penicillin, polymixin B, and colistin. The antibiotic may be selected from TABLE 2.

In a further embodiment of the invention, disrupting the cell wall is accomplished with one or more agents selected from the group of antibiotics, anti-microbial peptides, polycationic peptides, cell wall degrading enzymes, and catalytic antibodies.

The invention provides a method for modulation of sortase in gram-positive bacteria comprising disrupting the cell wall of the bacteria by administration of a cell wall disrupting agent such that the sortase is rendered more accessible and sensitive to a modifying, modulating or binding agent, and concomitant or serial administration of a sortase modifying, modulating or binding agent.

Gram positive bacteria are known and can readily be identified and may be selected from *Actinomyces, Bacillus, Listeria, Lactococcus, Staphylococcus, Streptococcus, Enterococcus, Mycobacterium, Corynebacterium,* and *Clostridium.*

In one aspect, the modifying, modulating or binding agent is an antibody or fragment thereof directed against sortase.

In a particular such method for inhibition of a cell membrane target protein, the cell wall disrupting agent is selected from the group of antibiotics, anti-microbial peptides, polycationic peptides, cell wall degrading enzymes, and catalytic antibodies. In a particular such method for inhibition of sortase, the cell wall disrupting agent is selected from the group of antibiotics, anti-microbial peptides, polycationic peptides, cell wall degrading enzymes, and catalytic antibodies.

The invention includes a method for modulation of a gram-positive bacteria cell wall or cell membrane target in a gram-positive bacteria, wherein said target is relatively inaccessible or insensitive to modifying or modulating agents, comprising subjecting the bacteria to a modifying or modulating agent that is less than about 70 KDa in size and greater than molecular weight of 1,200, such that said agent traverses the cell wall but does not diffuse through the cell wall, wherein said modifying or modulating agent is selected from an antibody or fragment thereof.

In this method, the cell wall or cell membrane target may be sortase. The modifying or modulating agent may be selected from an antibody or fragment thereof, a ligand, a bioactive peptide and an enzyme.

The present invention provides a method of treatment or amelioration of a gram-positive bacterial infection in a mammal comprising administering to said mammal one or more cell wall disrupting agent and a modifying or modulating agent targeting or selective for a cell wall or cell membrane target, wherein the modifying or modulating agent does not significantly inhibit the bacterial infection in the absence of the cell wall disrupting agent. The present invention provides a method of treatment or amelioration of a gram-positive bacterial infection in a mammal comprising administering to said mammal one or more cell wall disrupting agent and a modifying or modulating agent targeting or selective for a cell wall or cell membrane target, wherein the modifying or modulating agent more significantly and effectively inhibits the growth of the bacteria and ameliorates the bacterial infection in the presence of the cell wall disrupting agent than in the absence of the cell wall disrupting agent.

In an aspect of this method, the modifying, modulating or binding agent is an antibody or fragment thereof. In a further aspect of this method, the modifying, modulating or binding agent is selected from a ligand, a bioactive peptide, and an enzyme. In an aspect of the method, the cell wall or cell membrane target is sortase. In a further aspect, the cell wall or cell membrane target is selected from a penicillin binding protein, an ABC transporter, a potassium channel, a pore protein or pore component, β-lactamase, or other bacterial protein(s) that influence or are required for growth, virulence or resistance to antibiotic treatment. In an additional aspect, the cell wall or cell membrane target is selected from a sortase, a penicillin binding protein, an ABC transporter, a potassium channel protein and a surface factor promoting resistance to oxidative killing. In an aspect, the cell wall or cell membrane target is further selected from Table 1.

Disrupting the cell wall may be accomplished using one or more agents selected from the group of antibiotics, anti-microbial peptides, polycationic peptides, cell wall degrading enzymes, non-catalytic antibodies, and catalytic antibodies. In a particular aspect, the cell wall disrupting agent is an antibiotic. The cell wall disrupting agent(s) may have inherent antibacterial activity. The cell disrupting agent may be utilized at a concentration which is less than the minimally inhibitory concentration (MIC) of said agent, or at a concentration which is at or above the MIC of said agent.

The present invention provides a method of inhibiting or preventing growth of a gram positive bacteria by contacting said bacteria with one or more cell wall and/or cell membrane disrupter and one or more target modifying, modulating or binding agent. In a particular aspect of the method gram positive bacteria is contacted with a sub-MIC dose or quantity of one or more antibiotic and with one or more antibody directed to a cell membrane target. In a particular aspect of the method, gram positive bacteria is contacted with a sub-MIC dose or quantity of one or more antibiotic and with one or more antibody against sortase. In a further such aspect, gram positive bacteria is contacted with a sub-MIC dose or quantity of one or more antibiotic affecting cell wall biosynthesis and with one or more antibody against sortase. In a particular aspect, gram positive bacteria is contacted with a sub-MIC dose of one or more penicillin antibiotic in combination with an antibody directed against sortase.

The invention provides pharmaceutical and therapeutic compositions comprising one or more cell wall and/or cell membrane disrupter and one or more target modifying, modulating or binding agent. The disrupter(s) and agent(s) can be prepared in pharmaceutical compositions, including a suitable vehicle, carrier or diluent, for administration in instances wherein a gram-positive bacterial infection is diagnosed or determined or in an individual, particularly a compromised individual, at risk of infection or exposed to infection. Such pharmaceutical compositions may further comprise additional antibacterial agents, antibodies or therapeutic agents. Individual compositions or an agent and of a disrupter may be prepared separately and administered concurrently, in combination, or in sequence.

In an aspect of the invention, compositions are provided comprising an antibiotic and an antibody. Alternatively, compositions comprising a sub-MIC dose of an antibiotic are provided and compositions comprising a cell membrane target antibody, such as an anti-sortase antibody, are provided and may be administered concomitantly or separately, such as in succession, to an individual suffering from or at risk of a gram-positive bacterial infection. In a preferred aspect, the composition of disrupter and the composition of agent are administered such that both are present reasonably simultaneously so that they may act in combination on the susceptible bacteria.

A composition of the present invention may be administered alone or in combination with other treatments, therapeutics or agents, either simultaneously or sequentially dependent upon the condition to be treated. In addition, the present invention contemplates and includes compositions comprising the target agent, particularly antibody or fragment thereof, herein described and other agents or therapeutics such as antibiotic(s), anti-bacterial peptide(s), agents or therapeutics.

The invention includes an assay system for screening of potential drugs effective to modulate the accessibility of cell wall and/or cell membrane targets to antibodies or fragments thereof which traverse, penetrate or diffuse through the gram-positive bacterial cell wall poorly or not at all. The assay system may be for screening of potential drugs effective to modulate the accessibility of cell wall and/or cell membrane targets to ligands, enzymes, and other molecules which traverse, penetrate or diffuse through the gram-positive bacterial cell wall poorly and/or ineffectvely.

In an additional aspect, the present invention includes an assay system for isolating test agents or compounds capable of rendering a gram-positive bacterial cell wall and/or cell membrane target in a bacterial cell more sensitive to a target modifying, modulating or binding agent comprising contacting the bacterial cell with a test agent or compound in the presence of a target modifying, modulating or binding agent and assessing the activity of the target or binding of the binding agent to the target, wherein the binding of the binding agent to the target is increased and/or the activity of the target is modulated in the presence of the test agent when compared to the absence of test agent.

In the assay system, the cell wall and/or cell membrane target may be a sortase. In a further aspect of the assay system, the cell wall and/or cell membrane target may be selected from a sortase, penicillin binding protein, a pore protein or pore component, ABC transporter, β-lactamase, or other bacterial protein(s) that influence or are required for growth, virulence or resistance to antibiotics. The modifying, modulating or binding agent may be an antibody or fragment thereof. In an aspect of the assay system, the modifying, modulating or binding agent may be selected from an antibody or fragment thereof, a ligand, a bioactive peptide, and an enzyme.

In one embodiment of the assay system, the target is sortase and the activity of sortase and/or the binding of the binding agent to sortase is determined by assessing the activity or bacterial cell wall localization of a cell wall surface protein selected from protein A, fibronectin-binding protein, clumping factor, Sas protein and Sdr protein. In an aspect of the assay system, the target is a sortase, penicillin binding protein, ABC transporter, channel protein, surface factor, or other bacterial cell wall or cell membrane protein that influences or is required for growth, virulence or resistance to antibiotic(s). In an aspect of the assay system, the target is selected from a sortase, a penicillin binding protein, an ABC transporter, a potassium channel protein and a surface factor promoting resistance to oxidative killing. In an aspect of the assay system, the target is further selected from Table 1.

Other objects and advantages will become apparent to those skilled in the art from a review of the following description which proceeds with reference to the following illustrative drawings.

BRIEF DESCRIPTION OF THE DRAWINGS

FIG. 3B is an 4× enlargement of FIG. 3A.

FIGS. 6A and 6B depicts the nucleotide sequence (SEQ ID NO: 7) of the vector pAR203.

DETAILED DESCRIPTION

Figure 1:
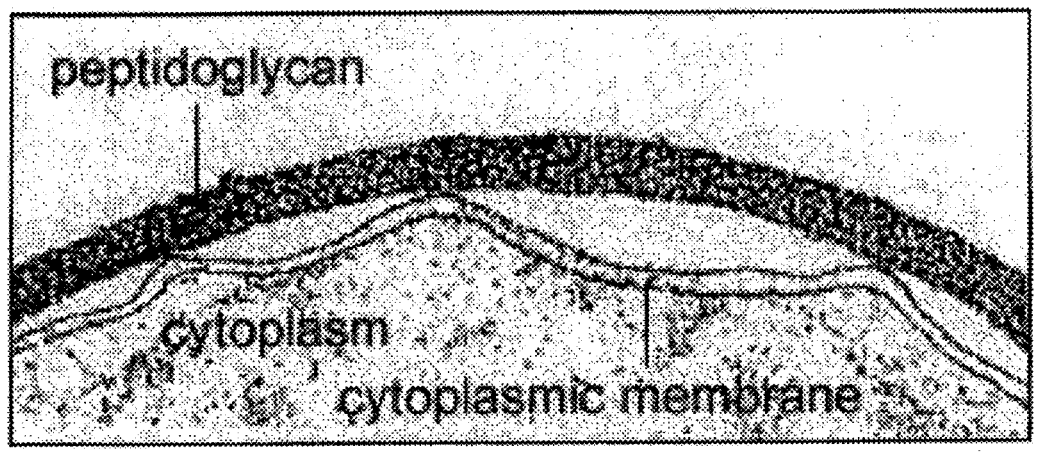
FIG. 1 depicts an electron micrograph of a gram-positive cell wall.
Figure 2:
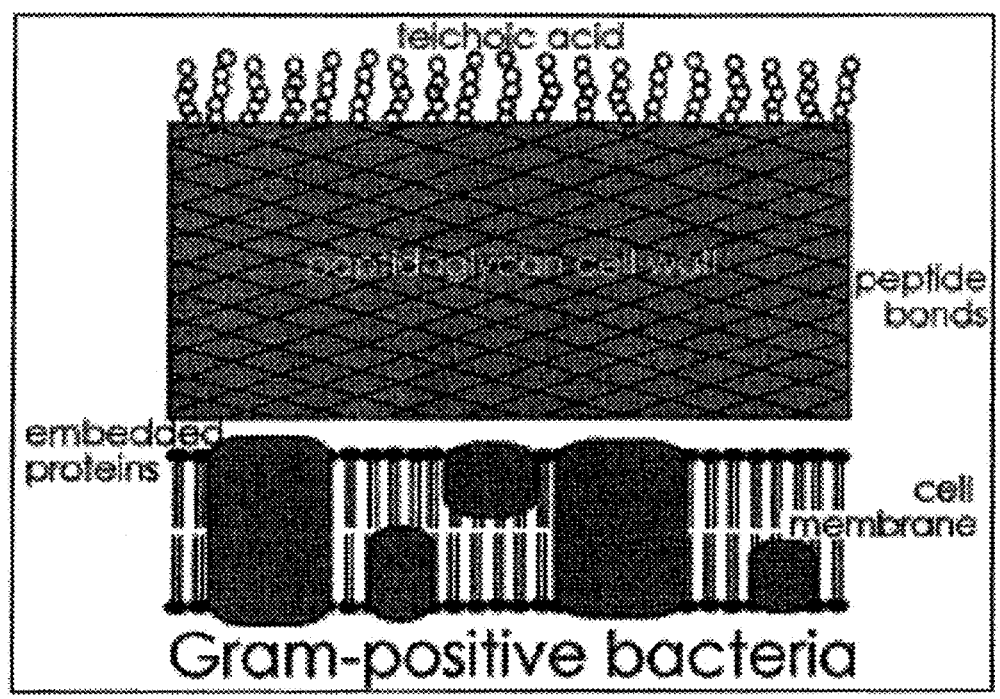
FIG. 2 depicts the structure of a bacterial cell wall.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

The terms "gram-positive bacteria", "Gram-positive bacteria", "gram-positive" and any variants not specifically listed, may be used herein interchangeably, and as used throughout the present application and claims refer to Gram-positive bacteria which are known and/or can be identified by the presence of certain cell wall and/or cell membrane characteristics and/or by staining with Gram stain. Gram positive bacteria are known and can readily be identified and may be selected from but are not limited to the genera *Actinomyces, Bacillus, Listeria, Lactococcus, Staphylococcus, Streptococcus, Enterococcus, Mycobacterium, Corynebacterium*, and *Clostridium*, and include any and all recognized or unrecognized species or strains thereof.

The term "bacteriocidal" refers to capable of killing bacterial cells.

The term "bacteriostatic" refers to capable of inhibiting bacterial growth, including inhibiting growing bacterial cells.

A "signal sequence" can be included at or near the beginning of the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

Two amino acid sequences are "substantially homologous" when at least about 70% of the amino acid residues (preferably at least about 80%, and most preferably at least about 90 or 95%) are identical, or represent conservative substitutions.

An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies. Immunoglobulin molecules can be of any class (e.g., IgG, IgE, IgM, IgD, IgA, and IgY), or subclass (e.g., IgG1, IgG2, IgG3, IgG4, IgA1, and IgA2). In addition, the term antibodies encompasses protein molecules derived from phage display or de novo synthesis of a polypeptide sequence substantially similar to antibodies as defined above or as provided herein, or polypeptides derived from synthetic genes coding for polypeptides substantially similar to antibodies as defined above or as provided herein. Also included within the meaning of the term "antibody" are any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH I) domains; (ii) a F(ab')2 fragment, which is a bivalent fragment comprising two Fab fragments linked by a disulfide bridge at the hinge region; (iii) a heavy chain portion of an Fab (Fd) fragment, which consists of the VH and CHI domains; (iv) a variable fragment (Fv) fragment, which consists of the VL and VH domains of a single arm of an antibody, (v) a domain antibody (dAb) fragment, which comprises a single variable domain; (vi) a camelid antibody; (vii) an isolated complementarity determining region (CDR); (viii) a Single Chain Fv Fragment; (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites; and (x) a linear antibody, which comprises a pair of tandem Fv segments (VH-CH1-VH-CH1) which, together with complementarity light chain polypeptides, form a pair of antigen binding regions; and (xi) other non-full length portions of heavy and/or light chains, or mutants, variants, or derivatives thereof, alone or in any combination.

An "antibody combining site" is that structural portion of an antibody molecule comprised of heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Fab and F(ab')$_2$ portions of antibody molecules are prepared by the proteolytic reaction of papain and pepsin, respectively, on substantially intact antibody molecules by methods that are well-known. See for example, U.S. Pat. No. 4,342,566 to Theofilopolous et al. Fab' antibody molecule portions are also well-known and are produced from F(ab')$_2$ portions followed by reduction of the disulfide bonds linking the two heavy chain portions as with mercaptoethanol, and followed by alkylation of the resulting protein mercaptan with a reagent such as iodoacetamide. An antibody containing intact antibody molecules is preferred herein.

It has been shown that fragments of a whole antibody can perform the function of binding antigens. Examples of binding fragments are (i) the Fab fragment consisting of VL, VH, CL and CHI domains; (ii) the Fd fragment consisting of the VH and CHI domains; (iii) the Fv fragment consisting of the VL and VH domains of a single antibody; (iv) the dAb fragment (Ward, E. S. et al., Nature 341, 544-546 (1989)) which consists of a VII domain; (v) isolated CDR regions; (vi) F(ab')2 fragments, a bivalent fragment comprising two linked Fab fragments (vii) single chain Fv molecules (scFv), wherein a VII domain and a VL domain are linked by a peptide linker which allows the two domains to associate to form an antigen binding site (Bird et al, Science, 242, 423-426, 1988; Huston et al, PNAS USA, 85, 5879-5883, 1988); (viii) multivalent antibody fragments (scFv dimers, trimers and/or tetramers (Power and Hudson, J Immunol. Methods 242: 193-204 9 (2000))(ix) bispecific single chain Fv dimers (PCT/US92/09965) and (x) "diabodies", multivalent or multispecific fragments constructed by gene fusion (WO94/13804; P. Holliger et al Proc. Natl. Acad. Sci. USA 90 6444-6448, (1993)).

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-bacterial protein antibody, for instance anti-sortase antibody or anti-PBP antibody. The other binding domain may be an antibody that recognizes or targets a particular bacterial cell type, as in a *Staphylococcal* cell-specific antibody. In the bispecific antibodies of the present invention the one binding domain of the antibody of the invention may be combined with other binding domains or molecules which recognize particular bacterial cell components or proteins and/or modulate cells in a particular fashion, as for instance an immune modulator (e.g., interleukin(s)), a motility modulator, a growth modulator, an antibacterial agent or antibiotic, a toxin (e.g., ricin) or anti-mitotic.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may therefore contain an antibody molecule having a plurality of antibody combining sites, each immunospecific for a different antigen; e.g., a bispecific (chimeric) monoclonal antibody.

The general methodology for making monoclonal antibodies by hybridomas or selection from phage or antibody libraries is well known and can be readily undertaken by one of skill in the art. Immortal, antibody-producing cell lines can also be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies And T-cell Hybridomas" (1981); Kennett et al., "Monoclonal Antibodies" (1980); see also U.S. Pat. Nos. 4,341,761; 4,399,121; 4,427,783; 4,444,887; 4,451,570; 4,466,917; 4,472,500; 4,491,632; 4,493,890.

Panels of monoclonal antibodies produced against cell wall and/or cell membrane target peptides can be screened for various properties; i.e., isotype, epitope, affinity, etc. Of particular interest are monoclonal antibodies that neutralize the activity of the cell wall and/or cell membrane target, such as a sortase, a PBP, an ABC transporter, etc or its subunits. Such monoclonals can be readily identified in activity assays or sorting assays, or by assessing surface proteins. The sequences of many such bacterial gram-positive cell membrane proteins are known and available. For example, some exemplary cell membrane proteins are indicated in Table 1 and Uniprot numbers are indicated, which may be utilized to identify available protein and/or nucleotide sequences for expressing the suitable protein(s) and generating antibodies thereto.

An antibody's binding and antigen recognition is largely, even sufficiently, determined by its Complementarity determining regions (CDR), which are the antibody regions of an immunoglobulin variable domain that determine specific antibody binding and where the molecule complements an antigen's conformation. Thus, CDRs, comprising CDR1, CDR2 and CDR3, determine the molecule's specificity and make contact with a specific antigen. CDR3 is the most variable.

In general, the CDR regions are carried in a structure which allows for binding of the CDR regions to the target antigen. The structure for carrying the CDRs of the invention will generally be of an antibody heavy or light chain sequence or substantial portion thereof in which the CDR regions are located at locations corresponding to the CDR region of naturally occurring VH and VL antibody variable domains encoded by rearranged immunoglobulin genes. The structures and locations of immunoglobulin variable domains may be determined by reference to Kabat, E. A. et al, Sequences of Proteins of Immunological Interest. 4th Edition. US Department of Health and Human Services. 1987, and updates thereof available on the Internet (immuno.bme.nwu.edu). The variable domains may be derived from any germline or rearranged human variable domain, or may be a synthetic variable domain based on consensus sequences of known human variable domains. The CDR-derived sequences of an antibody of use in the invention may be introduced into a repertoire of variable domains lacking CDR regions, using recombinant DNA technology.

Substitutions may be made in the variable region sequence outside of the CDRs so as to retain the CDR sequences. Thus, changes in the variable region sequence or alternative non-homologous or veneered variable region sequences may be introduced or utilized, such that the CDR sequences are maintained and the remainder of the variable region sequence may be substituted. Alternatively, substitutions may be made particularly in the CDRs.

For example, Marks et al (Bio/Technology, 1992, 10:779-783) describe methods of producing repertoires of antibody variable domains in which consensus primers directed at or adjacent to the 5' end of the variable domain area are used in conjunction with consensus primers to the third framework region of human VH genes to provide a repertoire of VH variable domains lacking a CDR/CDRs. Marks et al further describe how this repertoire may be combined with a CDR of a particular antibody. The repertoire may then be displayed in a suitable host system such as the phage display system of WO92/01047 so that suitable specific binding members may be selected. A repertoire may consist of from anything from $10^4$ individual members upwards, for example from $10^6$ to $10^8$ or $10^{10}$ members. Analogous shuffling or combinatorial techniques are also disclosed by Stemmer (Nature, 1994, 370:389-391), who describes the technique in relation to a β-lactamase gene but observes that the approach may be used for the generation of antibodies.

A further alternative is to generate novel VH or VL regions carrying the CDR-derived sequences of the invention using random mutagenesis of, for example, the Ab VH or VL genes to generate mutations within the entire variable domain. Such a technique is described by Gram et al (1992, Proc. Natl. Acad. Sci., USA, 89:3576-3580), who used error-prone PCR. Another method which may be used is to direct mutagenesis to CDR regions of VH or VL genes. Such techniques are disclosed by Barbas et al, (1994, Proc. Natl. Acad. Sci., USA, 91:3809-3813) and Schier et al (1996, J. Mol. Biol. 263:551-567).

A substantial portion of an immunoglobulin variable domain will comprise at least the three CDR regions, together with their intervening framework regions. Preferably, the portion will also include at least about 50% of either or both of the first and fourth framework regions, the 50% being the C-terminal 50% of the first framework region and the N-terminal 50% of the fourth framework region. Additional residues at the N-terminal or C-terminal end of the substantial part of the variable domain may be those not normally associated with naturally occurring variable domain regions. For example, construction of antibodies use in the present invention made by recombinant DNA techniques may result in the introduction of N- or C-terminal residues encoded by linkers introduced to facilitate cloning or other manipulation steps. Other manipulation steps include the introduction of linkers to join variable domains of the invention to further protein sequences including immunoglobulin heavy chains, other variable domains (for example in the production of diabodies) or protein labels as provided herein and/or known to those of skill in the art.

Although in a preferred aspect of the invention antibodies comprise a pair of binding domains, single binding domains may be utilized in further aspects of the invention, since it is known that immunoglobulin VH domains are capable of binding target antigens in a specific manner. This may be achieved by phage display screening methods using the so-called hierarchical dual combinatorial approach as disclosed in U.S. Pat. No. 5,969,108 in which an individual colony containing either an H or L chain clone is used to infect a complete library of clones encoding the other chain (L or H) and the resulting two-chain specific binding member is selected in accordance with phage display techniques such as those described in that reference. This technique is also disclosed in Marks et al, ibid. Phage library and phage display selection systems and techniques are also provided herein.

Antibodies of use in the invention may further comprise antibody constant regions or parts thereof. For example, variable region(s) of an antibody may be attached at their C-terminal end to antibody light chain constant domains including human CK or Ck chains, preferably CX chains. Binsing domains or variable regions may be attached at their C-terminal end to all or part of an immunoglobulin heavy chain derived from any antibody isotype, e.g. IgG, IgA, IgE, IgD and IgM and any of the isotype sub-classes, particularly IgG1, IgG2b, and IgG4.

Fully human antibodies can be prepared by immunizing transgenic mice carrying large portions of the human immunoglobulin heavy and light chains. These mice, examples of such mice are the Xenomouse™ (Abgenix, Inc.) (U.S. Pat. Nos. 6,075,181 and 6,150,584), the HuMAb-Mouse™ (Medarex, Inc./GenPharm) (U.S. Pat. Nos. 5,545,806 and 5,569,825), the TransChromo Mouse™ (Kirin) and the KM Mouse™ (Medarex/Kirin), are well known within the art. Antibodies can then be prepared by, e.g. standard hybridoma technique or by phage display. These antibodies will then contain only fully human amino acid sequences. Fully human antibodies can also be generated using phage display from human libraries. Phage display may be performed using methods well known to the skilled artisan, and as provided herein as in Hoogenboom et al and Marks et al (Hoogenboom H R and Winter G. (1992) J Mol Biol. 227(2):381-8; Marks J D et al (1991) J Mol Biol. 222(3): 581-97; and also U.S. Pat. Nos. 5,885,793 and 5,969,108).

All the above described techniques are known as such in the art and in themselves do not form part of the present invention. The skilled person will be able to use such techniques to provide antibodies or active fragments thereof of use in the invention using routine methodology in the art.

Antibodies or antibody molecules, fragments or portions thereof, may carry a detectable or functional label. The antibodies or molecules may carry a radioactive label, such as the isotopes $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{121}$I, $^{125}$I, $^{131}$I, $^{111}$In, $^{211}$At, $^{198}$Au, $^{67}$Cu, $^{225}$Ac, $^{213}$Bi, $^{99}$Tc and $^{186}$Re. When radioactive labels are used, known currently available counting procedures may be utilized to identify and quantitate the specific binding members. The label may have inherent cytotoxicity or cell proliferation inhibition. In the instance where the label is an enzyme, detection may be accomplished by any of the presently utilized colorimetric, spectrophotometric, fluorospectrophotometric, amperometric or gasometric techniques known in the art.

Immunoconjugates or antibody fusion proteins of the present invention, wherein the antibodies, antibody molecules, or fragments thereof, of use in the present invention are conjugated or attached to other molecules or agents further include, but are not limited to such antibodies, molecules, or fragments conjugated to a chemical ablation agent, toxin, immunomodulator, cytokine, cytotoxic agent, chemotherapeutic agent, antimicrobial agent or peptide, cell wall and/or cell membrane disrupter, or drug. The antibodies, or any fragments thereof, may be conjugated or recombinantly fused to any cellular toxin, bacterial or other, e.g. pseudomonas exotoxin, ricin, or diphtheria toxin. The part of the toxin used can be the whole toxin, or any particular domain of the toxin. Such antibody-toxin molecules have successfully been used for targeting and therapy of different kinds of cancers, see e.g. Pastan, Biochim Biophys Acta. 1997 Oct. 24; 1333(2):C1-6; Kreitman et al., N Engl J Med. 2001 Jul. 26; 345(4):241-7; Schnell et al., Leukemia. 2000 January; 14(1):129-35; Ghetie et al., Mol Biotechnol. 2001 July; 18(3):25 1-68. Bi- and tri-specific multimers can be formed by association of different scFv molecules and have been designed as cross-linking reagents for T-cell recruitment into tumors (immunotherapy), viral retargeting (gene therapy) and as red blood cell agglutination reagents (immunodiagnostics), see e.g. Todorovska et al., J Immunol Methods. 2001 Feb. 1; 248(1-2):47-66; Tomlinson et al., Methods Enzymol. 2000; 326:461-79; McCall et al., J Immunol. 2001 May 15; 166(10):61 12-7.

Peptides of and of use in the present invention may include synthetic, recombinant or peptidomimetic entitites. The peptides may be monomers, polymers, multimers, dendrimers, concatamers of various forms known or contemplated in the art, and may be so modified or mutlimerized so as to improve activity, specificity or stability. For instance, and not by way of limitation, several strategies have been pursued in efforts to increase the effectiveness of antimicrobial peptides including dendrimers and altered amino acids (Tarn, J. P. et al (2002) Eur J Biochem 269 (3): 923-932; Janiszewska, J. et al (2003) Bioorg Med Chem Lett 13 (21):371 1-3713; Ghadiri et al. (2004) Nature 369(6478):30 1-304; DeGrado et al (2003) Protein Science 12(4):647-665; Tew et al. (2002) PNAS 99(8):5 110-51 14; Janiszewska, J et al (2003) Bioorg Med Chem Lett 13 (21): 371 1-3713). U.S. Pat. No. 5,229,490 to Tarn discloses a particular polymeric construction formed by the binding of multiple antigens to a dendritic core or backbone.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense.

The term 'assay' means any process used to measure a specific property of a compound. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, or pharmaceutical agent that will elicit the biological or medical response of a subject that is being sought by a medical doctor or other clinician. In particular, with regard to gram-positive bacterial infections and growth of gram-positive bacteria, the term "effective amount" is intended to include an effective amount of a compound or agent that will bring about a biologically meaningful decrease in the amount of or extent of infection of gram-positive bacteria, including having a bacteriocidal and/or bacteriostatic effect. The phrase "therapeutically effective amount" is used herein to mean an amount sufficient to prevent, and preferably reduce by at least about 30 percent, more preferably by at least 50 percent, most preferably by at least 90 percent, a clinically significant change in the growth or amount of infectious bacteria, or other feature of pathology such as for example, elevated fever or white cell count as may attend its presence and activity.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, "pg" means picogram, "ng" means nanogram, "ug" or "^g" mean microgram, "mg" means milligram, "ul" or "µl" mean microliter, "ml" means milliliter, "l" means liter.

In its primary aspect, the present invention provides a means, methods and compositions for facilitating and/or mediating the modulation of bacterial target(s), particularly gram-positive bacterial targets, which are poorly accessible or insufficiently accessible to certain agents or molecules, and/or for enhancing the effectiveness of therapeutic agents.

In the present invention, the gram-positive bacterial cell, particularly the cell wall and/or outer surface of the bacteria, is disrupted such that peptides, enzymes or molecules embedded in or otherwise associated with the cell wall or cell membrane, particularly including sortase and/or sortase-family enzymes, including penicillin binding protein(s), transporter proteins, and relatively inaccessible or insufficiently sensitive to certain therapeutic molecules, particularly including antibodies and antibody fragments, are exposed or rendered sensitive or more accessible to modulation, binding, and/or recognition by antibodies, antibody fragments, or other therapeutic molecules.

In the present invention, upon disrupting the gram-positive bacterial cell, particularly the cell wall and/or outer surface of the bacteria, peptides, enzymes or molecules embedded in or otherwise associated with the cell wall or cell membrane are exposed or rendered sensitive/more accessible to therapeutic molecules, particularly binding molecules or agents, including ligands, enzymes, and other non-antibody based binding molecules, such as ankyrins, which have affinity and specificity for the exposed cell wall or cell membrane targets (Binz H K et al. (2004) Nat Biotechnol. 22(5):575-82).

The invention provides a method for modulation of one or more gram-positive bacterial cell targets in a gram-positive bacteria comprising disrupting the cell wall and/or peptidoglycan such that the target, particularly located within or beneath the cell wall, including in the cell membrane, associated with the cell membrane, or in the periplasmic space, is rendered exposed or more accessible and sensitive to a modifying, modulating or binding agent, wherein the target is inaccessible or relatively insensitive to the modifying, modulating or binding agent in the absence of cell wall disruption. In a further aspect the invention provides a method for modulation of one or more gram-positive bacterial cell targets in a gram-positive bacteria comprising disrupting the cell wall and/or peptidoglycan such that the target, particularly located within or beneath the cell wall, including in the cell membrane, associated with the cell membrane, or in the periplasmic space, is rendered more exposed or more accessible and more sensitive to a modifying, modulating or binding agent, wherein the target is less accessible or less sensitive to the modifying, modulating or binding agent in the absence of cell wall disruption. Thus, the invention provides a method for modulation of one or more gram-positive bacterial cell wall or cell membrane targets in a gram-positive bacteria comprising disrupting the cell wall such that the cell wall or cell membrane target is rendered exposed or accessible and sensitive to a modifying, modulating or binding agent, wherein the cell wall or cell membrane target is inaccessible or relatively insensitive to the modifying, modulating or binding agent in the absence of cell wall disruption. Gram positive bacteria are known and can readily be identified and may be selected from *Actinomyces, Bacillus, Listeria, Lactococcus, Staphylococcus, Streptococcus, Enterococcus, Mycobacterium, Corynebacterium*, and *Clostridium*. In a particular aspect the target bacteria is a clinically or medically significant genus or strain.

The present invention contemplates the use or application of the method of the invention to specifically and particularly target cell membrane proteins or components or such other proteins or components which are located inside the cell wall or interior to the peptidoglycan layer. As exemplified herein, antibiotics, such as penicillin, ampicillin, etc serve to permit or enable enhanced targeting of antibody(ies) to a cell membrane target. Thus, combinations of ampicillin or penicillin, for example, with an anti-sortase antibody enable the targeting and specific interaction of the anti-sortase antibody with its sortase target, such that sufficient antibody to generate an immunofluorescence signal reaches the sortase target on the cell membrane. In the absence of the antibiotic, in this instance, insufficient amount(s) of anti-sortase antibody reaches the cell membrane sortase target to generate an immunofluorsencence signal. The combination of cell disrupter antibiotic with cell membrane protein target antibody provides a vehicle or method for delivering label (fluorophore, dye, etc) to the cell membrane target. Thus, a delivery method is provided for targeting antibodies, or other entities attached to or bound to said antibody, for instance, to a cell membrane target or such other target inside the cell wall or across the peptidoglycan layer. It is contemplated that labels, toxins, ligands, antagonists, agonists, peptides, etc can be delivered to a cell membrane target or such other target inside the cell wall or across the peptidoglycan layer via the present method, and thus via a combination of cell wall disrupter (such as an antibiotic) and bacterial cell membrane protein target agent (such as an antibody or an antibody covalently or non-covalently associated with a bioactive peptide or a toxin).

The invention thus provides delivery and targeting methods directed to gram positive cell membrane proteins. The method may be utilized to characterize or assess the role or function of a target protein in bacterial cell growth or virulence, by delivering agents or inhibitors effectively as could not readily be achieved previously. Assays to assess inhibition or inactivation of one or more cell membrane protein target are thus provided.

Currently, 65% of *Staphylococcal* bacteria encountered in the hospital are drug-resistant (MRSA), causing serious, if not fatal, infections. One of these MRSA strains has now become a major pathogen in the community where it has also emerged as a sexually-transmitted infection in homosexual men. Due to this increased occurrence of resistant pathogens in the hospital and community, it is necessary, if not imperative, to develop new therapeutic approaches.

Antibodies play a major role in protection against pathogens. Antibodies can be induced by vaccination or transferred passively from one animal to another with immune sera. In fact, more than thirteen life-threatening infections have been brought under control through the development and routine use of vaccines. While vaccines have eliminated some of the most devastating diseases known, the use and applicability of directly transferred antibody for control of infection has remained limited. Instead, it was the discovery of potent antibiotics and antiviral compounds that provided the accepted treatment option(s) for bacteria and viruses in the doctor's office and hospital.

The broad uses of antibiotics in industrial scale farming and in human therapeutics have provided potent selective pressures that have resulted in a high proportion of antibiotic resistant pathogens in the environment. The escape mechanisms employed by pathogens are diverse, including enzymes that cleave and render antibiotics ineffective, transport systems that remove antibiotics from their sites of action, mutations that alter the target sites for therapy, replicative mechanisms that allow for extremely high levels of mutation or genetic reassortment, and the transfer of these resistance factors from one organism to another. Koch (Koch A L (2003) Clin Microbiol Rev 16(4):673-687) argues that if a therapeutic target can be chosen that has not been exploited in nature, as were the β-lactamases, then the bacterial response will be slow because lateral gene transfer cannot function and a countermeasure will arise only as a result of rare or multiple accumulation of mutations.

In contrast to drugs, antibodies exist naturally in the blood and their levels vary according to the immune response to different antigens. They are essentially neutral proteins that circulate in serum until they bind to antigen and become activated. Mabs are injectable or they can be administered intravenously. They have a rapid onset of efficacy and serum half-life varies from 9-21 days depending upon the subtype of the Mab. This half-life can be compared to those of pharmaceuticals which are generally measured in hours. Moreover, the specificity and affinity of antibodies exceed that of synthetic drugs by hundreds to ten-thousand fold. This is magnified by the increased potency of Mabs due to their avidity. Further, the mechanisms of action of antibodies follow known principles and recent technologies have been developed to further potentiate antibodies by several orders of magnitude.

Exemplary Bacterial Targets for Modulation

Sortases

In *S. aureus* alone, over 20 cell wall-anchored proteins with sorting motifs (including LPXTG) have been identified, including Protein A, fibronectin binding proteins, clumping factors, and various surface proteins with unknown functions (such as Sas proteins and Sdr proteins) (Marraffini, L A et al (2006) Microbial Mol Bio Rev 70(1): 192-221). Sortase A (SrtA) of *S. aureus* is 206 amino acids with an N-terminal membrane spanning region and a C-terminal catalytic domain (Mazmanian S K et al (1999) Science 285:760-763). Sortase mutants display severe defects in the pathogenesis of animal infections (Jonsson IM et al (2002) J Infect Dis 185:1417-1424; Johnsson I M et al (2003) Microb Infect 5:775-780).

The crystal structure of *S. aureus* sortase A and a substrate complex, LPETG (SEQ ID NO: 6) peptide, has been determined (Zong Y et al (2004) J Biol Chem 279(30):31383-31389). The sortase A gene of *S. aureus* has been cloned and its protein and nucleic acid sequence determined (Mazmanian S K et al (1999) Science 285:760-763) and it is described in U.S. Pat. No. 6,773,706, incorporated herein in its entirety by reference.

Because of the central role of sortases in the functional assembly of the cell wall envelope and surface protein anchoring and in bacterial pathogenicity, sortases are recognized as a target for the development of therapeutic agents that may disrupt human infections caused by Gram-positive bacteria (Cossart, P. and Jonquieres, R. (2000) PNAS 97:5013-5015).

Comfort and Clubb have undertaken a comparative genome analysis identifying and analyzing the multiple sortase genes and their associated pathways in gram-positive bacteria (Comfort, D. and Clubb, R. T. (2004) Infec Immunol 72(5):27 10-2732). The sortase enzymes are classified into five distinct subfamilies, which are predicted to function non-redundantly and vary in their primary sequences and/or substrates. The functional sortase-substrate linkages are available in a searchable website database (nihserver.mbi.ucla.edu/Sortase). Various sortase-family members and sortase like peptides have been identified, sequenced, characterized, and their substrates determined in numerous gram-positive bacteria and are known and publicly available.

An additional feature of sortases is their involvement in the formation of pili, or fimbriae, in gram-positive bacteria, including *Actinomyces, Corynebacterium* and *Streptococcus*). Pili are assembled in the cell wall envelope and protrude from the microbial surface and perform important functions in bacterial pathogenesis (Ton-That, H. and Schneewind, O. (2004) Trends Microbiol 12:228-234; Marraffini, L A et al (2006) Microbial Mol Bio Rev 70(1):192-221).

Small molecules and chemical or synthetic compounds have been evaluated for sortase inhibition. Methane-thiosulfonates such as MTSET and (2-sulfonatoethyl)methane-thiosulfonate inhibit sortase in vitro and in vivo and react with its catalytic and active site $Cys^{184}$ (Ton-That H and Schneewind O (1999) J Biol Chem 274(34):243 16-24320). However, the recognized non-discriminate interactions of thiol-reactive molecules renders the compounds inappropriate for therapeutic studies due to their associated toxicity in mammals Threonine mimics have been shown to inhibit sortase (Jung M E (2005) Bioorg Med Chem Lett 15(22): 5076-5079). Substrate and peptide mimics have also been evaluated as candidate sortase inhibitors (Lee H S et al (2005) J Nat Prod 68(4):623-625; Scott C J et al ((2002) J Biochem 366(Pt 3):953-958; Kruger R G et al (2004) 12(1 3):3723-3729). The development of resistance, toxicity associated with compound levels required for activity, non-specific nature of enzyme inhibitors inherently limit the applicability and long-term effectiveness of many of these more traditional molecules and compounds.

Antibodies to sortase have been generated or isolated and additional antibodies, including specific neutralizing antibodies and antibody molecules, can readily be generated, including based on the sequences and expression of known sortases or sortase family members from any of gram-positive bacteria. A rabbit anti-*S. aureus* sortase A polyclonal antibody ab 13959 is commercially available from Abcam.

Antibodies directed against *S. aureus* sortase A are described and utilized in the examples provided herein. Antibodies directed against sortase enzyme from other bacteria are known and have been described. These are utilized in additional experiments to further demonstrate antibiotic-enhancing effects with other cell membrane protein sortase-specific antibodies. Gaspar et al has described an antibody specific to *B. anthracis* sortase, tested by Western blot detection of the anthrax sortase (Gaspar A H et al., J Bacteriol 187: 13 (2005). Gianfaldoni and colleagues have described sortase as a vaccine antigen and that active transfer of anti-streptococcal pneumonia SrtA polyclonal antiserum confers resistance in mice (Gianfaldoni C et al., Infection and Immunity 77:7 (2009), 2957-296 1). The mechanism of action of the polyclonal serum and its component(s) is unclear. In particular, other studies have noted and underscored that the transpeptidase sortase A is not accessible to either protease or antibody on the bacterial surface (De Dent A. C. et al (2007) J B act 189(12):4473-4484). Fischetti has confirmed in fixed *S. pyogenes* cells that sortase is located at the cell membrane (Raz A and Fischetti V A (2008) PNAS 105(47): 18549-18554). The present studies additionally demonstrate that *S. aureus* sortase is not detectable by immunofluorescence with anti-sortase antibody in non-disrupted bacterial cells.

Other Targets

Below and protected by the cell wall is the bacterial cell membrane, which regulates the flow of materials in and out of the cell. Various important, if not essential bacterial proteins reside within or are associated with the cell membrane. Sortase is a membrane protein required for infection and the transport of key cell-wall and surface proteins, as above described and noted. Pores or channel-type facilitators cross the cell membrane and act as 'holes' or channels through which molecules can diffuse or be selectively transported. Pores are comprised of membrane spanning and membrane associated proteins, and these provide alternative targets for therapeutic modulation.

Penicillin binding protein (PBP) is a membrane-bound protein that covalently binds to penicillin, and is a transpeptidase naturally involved in cell wall generation and the cross-linking of cell wall peptides/peptidoglycans. Most bacteria have a small number of different kinds of PBPs. Methicillin-resistant *Staphylococcus aureus* (MRSA) has an additional PBP (PBP2') which binds poorly to β-lactamases but can still function in the synthesis of peptidoglycans. It would be beneficial to more readily access and target PBPs with new and specific molecules, including antibodies or other ligands or neutralizing agents. The cell-membrane location of PBPs, however, requires that such agents penetrate and traverse the cell wall to the cell membrane target PBP. The methods and compositions of the present invention thus provide for more readily and/or more effectively accessing and modulating PBPs, either more effectively with current therapies, using lower effective amounts of therapies, and/or using larger polypeptides, agents or molecules, such as and including antibodies and other macromolecules. Antibodies to PBPs have been generated or isolated and additional antibodies, including specific neutralizing antibodies and antibody molecules, can readily be generated, including based on the sequences and expression of known PBPs from any of gram-positive bacteria.

Various existing bacterial gram-positive cell membrane proteins are known and have been described and/or characterized. Exemplary cell membrane proteins are indicated in Table 1, including reference to their structure in the PDB structural database and their Uniprot designation which provides access to available nucleotide and/or protein sequences.

TABLE 1

BACTERIAL GRAM POSITIVE MEMBRANE PROTEINS

| Protein Name | PDB ID | UNIProt | Species | Num. Subunits | Num. TM Structs. | Hydrophobic Thickness or Depth (A) |
|---|---|---|---|---|---|---|
| Porin MspA | 1uun | Q9RLP7 | Mycobacterium smegmatis | 8 | 16 | 54.2 ± 0.9 |
| Glycosyltransferase MtgA | 3hzs | Q7A016 | Staphylococcus aureus | 1 | 0 | 6.8 ± 1.3 |
| Penicillin-binding protein 2 | 2olv | Q2YY56 | Staphylococcus aureus | 1 | 0 | 3.6 ± 1.0 |
| Antigen 85a | 1sfr | P0A4V2 | Mycobacterium tuberculosis | 1 | 0 | 3.4 ± 0.4 |
| Antigen 85c | 1dqz | P0A4V4 | Mycobacterium tuberculosis | 1 | 0 | 4.8 ± 0.5 |
| Antigen 85b | 1f0n | P0C5B9 | Mycobacterium tuberculosis | 1 | 0 | 3.7 ± 0.6 |
| FIFO ATP synthase subunit c | 1wuO | P00845 | Bacillus ps3 | 1 | 2 | 30.6 ± 3.4 |
| FIFO ATP synthase | 2x2v | P22483 | Bacillus pseudofirmus | 13 | 26 | 37.4 ± 0.6 |
| Multidrug ABC transporter SAV1866, closed state | 2hyd | Q99T13 | Staphylococcus aureus | 2 | 12 | 35.8 ± 1.3 |
| Sodium-hydantoin transporter Mhp 1, inward-facing conformation | 2x79 | | Mycobacterium liquefaciens | 1 | 12 | 29.8 ± 1.6 |
| Sodium-hydantoin transporter Mhpl, outward-facing conformation | 2jln | | Mycobacterium liquefaciens | 1 | 12 | 28.7 ± 1.1 |
| Sodium-hydantoin transporter Mhp 1, ligand-bound | 2jlo | | Mycobacterium liquefaciens | 1 | 12 | 31.8 ± 1.7 |
| Potassium channel KcsA, full-length, closed | 3eff | P0A334 | Streptomyces lividans | 12 | 12 | 34.0 ± 1.7 |
| Potassium channel KcsA, open 14.5 A conformer | 3fb5 | P0A334 | Streptomyces lividans | 4 | 8 | 34.2 ± 0.6 |
| Potassium channel KcsA, open 23A conformer | 3f7v | P0A334 | Streptomyces lividans | 4 | 8 | 29.7 ± 1.8 |
| Potassium channel KcsA | 1s5h | P0A334 | Streptomyces coelicolor | 4 | 12 | 34.8 ± 0.9 |
| Potassium channel KscA, complex with charibdotoxin | 2a9h | P0A334 | Streptomyces lividans | 4 | 8 | 34.8 ± 0.5 |
| Potassium channel KcsA | 1r3j | P0A334 | Streptomyces lividans | 4 | 12 | 35.3 ± 0.8 |
| NaK potassium channel, open state | 3e86 | Q8lHW2 | Bacillus cereus | 4 | 12 | 26.6 ± 1.0 |
| NaK potassium channel, closed state | 2ahy | Q8lHW2 | Bacillus cereus | 4 | 12 | 29.5 ± 0.8 |
| Potassium channel KcsA, open inactivated state | 3f5w | P0A334 | Streptomyces lividans | 4 | 8 | 28.9 ± 0.9 |
| Mechanosensitive channel MscL | 2oar | A5U127 | Mycobacterium tuberculosis | 5 | 10 | 36.7 ± 1.7 |
| Mechanosensitive channel MscL | 3hzq | P68806 | Staphylococcus aureus | 4 | 8 | 19.9 ± 0.9 |
| Squalene-hopene cyclase | 2sqc | P33247 | Alicyclobacillus acidocaldarius | 2 | 0 | 7.7 ± 0.2 |
| Septium site-determining protein DivIVA | 2wuj | P71021 | Bacillus subtilis | 2 | 0 | 4.0 ± 1.0 |
| Lipoprotein lppX | 2byo | P65306 | Mycobacterium tuberculosis | 1 | 0 | 1.4 ± 1.0 |
| Alpha-glycerophosphate oxidase (GlpO) | 2rgh | D0VWY7 | Streptococcus sp. | 1 | 0 | 3.8 ± 1.2 |
| Teichoic acid biosynthesis protein F | 3l7l | Q5HLM5 | Staphylococcus epidermidis | 1 | 0 | 6.9 ± 2.0 |
| Translocation ATPase SecA | 1tf5 | P28366 | Bacillus subtilis | 1 | 0 | 2.7 ± 1.3 |

TABLE 1-continued

BACTERIAL GRAM POSITIVE MEMBRANE PROTEINS

| Protein Name | PDB ID | UNIProt | Species | Num. Subunits | Num. TM Structs. | Hydrophobic Thickness or Depth (A) |
|---|---|---|---|---|---|---|
| Cholesterol oxidase | 1coy | P22637 | *Brevibacterium sterolicum* | 1 | 0 | 4.6 ± 1.3 |
| Cholesterol oxidase | 1b4v | P12676 | *Streptomyces sp.* | 1 | 0 | 5.6 ± 1.2 |
| Epoxide Hydrolase | 2bng | Q7TY00 | *Mycobacterium bovis* | 2 | 0 | 8.4 ± 0.4 |

Cell Wall and/or Membrane Disruption

In one aspect of the invention the cell wall and/or membrane is specifically disrupted so that molecules which cannot readily access or modulate their targets in gram-positive bacterial cell wall and/or cell membrane and/or between the cell wall and cell membrane are thereby able to better access or modulate/modify their embedded target(s). Cell wall and/or cell membrane disruption may be accomplished with disrupters which are known, can be generated, or can be screened as described herein. Disrupters may include, but not be limited to any or one or more antibiotics. Disrupters may include any one or more of antimicrobial peptides, polycationic peptides, cell-wall degrading enzymes, catalytic antibodies.

In an aspect of the invention a cell wall and/or membrane disrupter, such as an antimicrobial peptide or polycationic peptide may serve as a cell wall disrupter and/or as a target modulator, simultaneously and/or in combination with another disruptor or target modulator. Thus, it is anticipated that advantageous and combinatorial effects may be achieved by utilizing, for instance, an antibiotic, an antibody and an antimicrobial peptide in combination, which may not be achieved by any one or such agents alone.

Antibiotics

Antimicrobials act largely by interfering with the structure or function of a gram-positive bacterial cell by inhibition of cell wall synthesis, inhibition of cell-membrane function and/or inhibition of metabolic functions, including protein and DNA synthesis. Cell wall synthesis inhibitors, including penicillin and antibiotics like it, disrupt the rigid outer cell wall so that the relatively unsupported cell swells and eventually ruptures. Table 2 provides an exemplary list of antibiotics including their recognized mechanism of action.

TABLE 2

Antibiotics by Class

| Generic Name | Brand Names | Common Uses[2] | Possible Side Effects[1] | Mechanism of action |
|---|---|---|---|---|
| Ansamycins | | | | |
| Geldanamycin | | Experimental, as antitumor antibiotics | | |
| Herbimycin | | | | |
| Carbacephem | | | | |
| Loracarbef | Lorabid | | | prevents bacterial cell division by inhibiting cell wall synthesis. |
| Carbapenems | | | | |
| Ertapenem | Invanz | Bactericidal for both Gram-positive and Gram-negative organisms and therefore useful for empiric broad-spectrum antibacterial coverage. (Note MRSA resistance to this class.) | Gastrointestinal upset and diarrhea Nausea Seizures Headache Rash and Allergic reactions | Inhibition of cell wall synthesis |
| Doripenem | Finibax | | | |
| Imipenem/Cilastatin | Primaxin | | | |
| Meropenem | Merrem | | | |
| Cephalosporins (First generation) | | | | |
| Cefadroxil | Duricef | | Gastrointestinal upset and diarrhea Nausea (if alcohol taken concurrently) Allergic reactions | Same mode of action as other beta-lactam antibiotics: disrupt the synthesis of the peptidoglycan layer of bacterial cell walls. |
| Cefazolin | Ancef | | | |
| Cefalotin or Cefalothin | Keflin | | | |
| Cefalexin | Keflex | | | |
| Cephalosporins (Second generation) | | | | |
| Cefaclor | Ceclor | | Gastrointestinal upset and diarrhea Nausea (if alcohol taken concurrently) | Same mode of action as other beta-lactam antibiotics: disrupt the synthesis of the peptidoglycan layer |
| Cefamandole | Mandole | | | |
| Cefoxitin | Mefoxin | | | |
| Cefprozil | Cefzil | | | |

TABLE 2-continued

Antibiotics by Class

| Generic Name | Brand Names | Common Uses[2] | Possible Side Effects[1] | Mechanism of action |
|---|---|---|---|---|
| Cefuroxime | Ceftin, Zinnat | | Allergic reactions | of bacterial cell walls. |
| Cephalosporins (Third generation) | | | | |
| Cefixime | Suprax | | | Same mode of action as other beta-lactam antibiotics: disrupt the synthesis of the peptidoglycan layer of bacterial cell walls. |
| Cefdinir | Omnicef, Cefdiel | | | |
| Cefditoren | Spectracef | | Gastrointestinal upset and diarrhea | |
| Cefoperazone | Cefobid | | | |
| Cefotaxime | Claforan | | Nausea (if alcohol taken concurrently) | |
| Cefpodoxime | | | Allergic reactions | |
| Ceftazidime | Fortaz | | | |
| Ceftibuten | Cedax | | | |
| Ceftizoxime | | | | |
| Ceftriaxone | Rocephin | | | |
| Cephalosporins (Fourth generation) | | | | |
| Cefepime | Maxipime | | Gastrointestinal upset and diarrhea Nausea (if alcohol taken concurrently) Allergic reactions | Same mode of action as other beta-lactam antibiotics: disrupt the synthesis of the peptidoglycan layer of bacterial cell walls. |
| Cephalosporins (Fifth generation) | | | | |
| Ceftobiprole | | | Gastrointestinal upset and diarrhea Nausea (if alcohol taken concurrently) Allergic reactions | |
| Glycopeptides | | | | |
| Teicoplanin | | | | inhibiting peptidoglycan synthesis |
| Vancomycin | Vancocin | | | |
| Macrolides | | | | |
| Azithromycin | Zithromax, Sumamed, Zitrocin | | | inhibition of bacterial protein biosynthesis by binding irreversibly to the subunit 50S of the bacterial ribosome, thereby inhibiting translocation of peptidyl tRNA. |
| Clarithromycin | Biaxin | Streptococcal infections, syphilis, respiratory infections, mycoplasmal infections, Lyme disease | Nausea, vomiting, and diarrhea (especially at higher doses) Jaundice | |
| Dirithromycin | | | | |
| Erythromycin | Erythocin, Erythroped | | | |
| Roxithromycin | | | | |
| Troleandomycin | | | | |
| Telithromycin | Ketek | Pneumonia | Visual Disturbance, Liver Toxicity.[3] | |
| Spectinomycin | | Antimetabolite, Anticancer | | |
| Monobactams | | | | |
| Aztreonam | | | | Same mode of action as other beta-lactam antibiotics: disrupt the synthesis of the peptidoglycan layer of bacterial cell walls. |
| Penicillins | | | | |
| Amoxicillin | Novamox, Amoxil | Wide range of infections; penicillin used for streptococcal infections, syphilis, and Lyme disease | Gastrointestinal upset and diarrhea Allergy with serious anaphylactic reactions Brain and kidney damage (rare) | Same mode of action as other beta-lactam antibiotics: disrupt the synthesis of the peptidoglycan layer of bacterial cell walls. |
| Ampicillin | | | | |
| Azlocillin | | | | |
| Carbenicillin | | | | |
| Cloxacillin | | | | |
| Dicloxacillin | | | | |
| Flucloxacillin | Floxapen | | | |
| Mezlocillin | | | | |
| Meticillin | | | | |
| Nafcillin | | | | |
| Oxacillin | | | | |
| Penicillin | | | | |
| Piperacillin | | | | |
| Ticarcillin | | | | |

TABLE 2-continued

Antibiotics by Class

| Generic Name | Brand Names | Common Uses[2] | Possible Side Effects[1] | Mechanism of action |
|---|---|---|---|---|
| Polypeptides | | | | |
| Bacitracin | | Eye, ear or bladder infections; usually applied directly to the eye or inhaled into the lungs; rarely given by injection | Kidney and nerve damage (when given by injection) | Inhibits isoprenyl pyrophosphate, a molecule which carries the building blocks of the peptidoglycan bacterial cell wall outside of the inner membrane[4] |
| Colistin Polymyxin B | | | | Interact with the bacterial cytoplasmic membrane, changing its permeability. |
| Quinolones | | | | |
| Ciprofloxacin | Cipro, Ciproxin, Ciprobay | Urinary tract infections, bacterial prostatitis, community-acquired pneumonia, bacterial diarrhea, mycoplasmal infections, gonorrhea | Nausea (rare), tendinosis (rare) | inhibit the bacterial DNA gyrase or the topoisomerase IV enzyme, thereby inhibiting DNA replication and transcription. |
| Enoxacin | | | | |
| Gatifloxacin | Tequin | | | |
| Levofloxacin | Levaquin | | | |
| Lomefloxacin | | | | |
| Moxifloxacin | Avelox | | | |
| Norfloxacin | Noroxin | | | |
| Ofloxacin | Ocuflox | | | |
| Trovafloxacin | Trovan | | | |
| Sulfonamides | | | | |
| Mafenide | | Urinary tract infections (except sulfacetamide and mafenide); mafenide is used topically for burns | Nausea, vomiting, and diarrhea Allergy (including skin rashes) Crystals in urine Kidney failure Decrease in white blood cell count Sensitivity to sunlight | Folate synthesis inhibition. They are competitive inhibitors of the enzyme dihydropteroate synthetase, DHPS. DHPS catalyses the conversion of PABA (̂ara-aminobenzoate) to dihydropteroate, a key step in folate synthesis. Folate is necessary for the cell to synthesize nucleic acids (nucleic acids are essential building blocks of DNA and RNA), and in its absence cells will be unable to divide. |
| Prontosil (archaic) | | | | |
| Sulfacetamide | | | | |
| Sulfamethizole | | | | |
| Sulfanamide (archaic) | | | | |
| Sulfasalazine | | | | |
| Sulfisoxazole | | | | |
| Trimethoprim | | | | |
| Trimethoprim-Sulfamethoxazole (Co-trimoxazole) (TMP-SMX) | Bactrim | | | |
| Tetracyclines | | | | |
| Demeclocycline | | Syphilis, chlamydial infections, Lyme disease, mycoplasmal infections, acne rickettsial infections | Gastrointestinal upset Sensitivity to sunlight Staining of teeth (especially in children) Potential toxicity to mother and fetus during pregnancy | inhibiting the binding of aminoacyl-tRNA to the mRNA-ribosome complex. They do so mainly by binding to the 30S ribosomal subunit in the mRNA translation complex.[5] |
| Doxycycline | Vibramycin | | | |
| Minocycline | Minocin | | | |
| Oxytetracycline | Terracin | | | |
| Tetracycline | Sumycin | | | |
| Others | | | | |
| Arsphenamine | Salvarsan | Spirochaetal infections (obsolete) | | |
| Chloramphenicol | Chloromycetin | | | |
| Clindamycin | Cleocin | acne infections, prophylaxis before surgery | | |
| Lincomycin | | acne infections, prophylaxis before surgery | | |
| Ethambutol | | Antituberculosis | | |
| Fosfomycin | | | | |
| Fusidic acid | Fucidin | | | |
| Furazolidone | | | | |
| Isoniazid | | Antituberculosis | | |

TABLE 2-continued

Antibiotics by Class

| Generic Name | Brand Names | Common Uses[2] | Possible Side Effects[1] | Mechanism of action |
|---|---|---|---|---|
| Linezolid | Zyvox | | | |
| Metronidazole | Flagyl | Giardia | | |
| Mupirocin | Bactroban | | | |
| Nitrofurantoin | Macrodantin, Macrobid | | | |
| Platensimycin | | | | |
| Pyrazinamide | | Antituberculosis | | |
| Quinupristin/Dalfopristin | Syncercid | | | |
| Rifampicin (Rifampin in US) | | mostly Gram-positive and mycobacteria | Reddish-orange sweat, tears, and urine | Binds to the β subunit of RNA polymerase to inhibit transcription |
| Tinidazole | | | | |

References
[1]Pelczar, M. J., Chan, E.C.S. and Krieg, N. R. (1999) "Host-Parasite Interaction; Nonspecific Host Resistance", In: Microbiology Concepts and Applications, 6th ed., McGraw-Hill Inc., New York, U.S.A. pp. 478-479.
[2]For common Uses and possible side effects reference is: Robert Berkow (ed.) *The Merck Manual of Medical Information - Home Edition*. Pocket (September 1999), ISBN 0-671-02727-1.
[3]Splete, Heidi; Kerri Wachter (March 2006). "Liver toxicity reported with Ketek". *Internal Medicine News*.
[4]*Mechanism of Action of Bacitracin: Complexation with Metal Ion and C55-Isoprenyl Pyrophosphate* K. John Stone and Jack L. Strominger
[5]*Life-Extension-Drugs.com - Doxycycline*

Antibiotics can also be subgrouped broadly into those affecting cell wall peptidoglycan biosynthesis and those affecting DNA or protein synthesis in gram positive bacteria, such as as follows:

I. Antibiotics Affecting Cell Wall Peptidoglycan Biosynthesis of Gram Positive Bacteria 1. Glycopeptides—Inhibit peptidoglycan synthesis by preventing the incorporation of N-acetylmuramic acid (NAM) and N-acetylglucosamine (NAG) peptide subunits into the peptidoglycan matrix. Available glycopeptides include vancomycin and teicoplanin.
2. Penicillins—Act by inhibiting the formation of peptidoglycan cross-links. The functional group of penicillins, the β-lactam moiety, binds and inhibits DD-transpeptidase that links the peptidoglycan molecules in bacteria. Hydrolytic enzymes continue to break down the cell wall, causing cytolysis or death due to osmotic pressure. Common penicillins include oxacillin, ampicillin and cloxacillin.
3. Polypeptides—Interfere with the dephosphorylation of the Css-isoprenyl pyrophosphate, a molecule that carries peptidoglycan building-blocks outside of the plasma membrane. Cell wall-impacting polypeptide is bacitracin.

II. Antibiotics Inhibiting DNA or Protein Synthesis in Gram Positive Bacteria

1. Quinolones—Inhibit DNA replication and transcription by inhibiting the bacterial DNA gyrase or topoisomerase II. Common quinolones include ciprofloxacin and ofloxacin.
2. Macrolides—Inhibit protein synthesis by irreversibly binding the bacterial 50S ribosomal subunit. Common macrolides include azithromycin and erythromycin.
3. Sulfonamides—Competitively inhibit the enzyme dihydropteroate synthetase (DHPS), an enzyme involved in folate synthesis. Common sulfonamides include sulfisomidine and sulfadoxine.

The emergence of antibiotic resistant gram-positive strains of bacteria has resulted in the search for novel antibiotics which overcome or avoid the resistance. Telavancin is a lipoglycopeptide antibiotic with a multifunctional mechanism of action, disrupting both cell wall synthesis and membrane integrity in methicillin-resistant *S. aureus* (Higgins D L et al (2005) 49(3): 1 127-1 134). This and comparable emerging antibiotics are of particular application and use in the present invention.

Antibiotics that inhibit cell wall synthesis and/or cell membrane function, and particularly wherein the cell wall is compromised or disrupted are particularly of use in the present invention. The antibiotic may be administered at bacterially effective doses, thereby providing enhanced bacterial inhibition. In an embodiment of the invention, the cell wall and/or outer surface of the bacteria is disrupted but not to a degree wherein this disruption has a significant antimicrobial effect such that the growth or virulence is disrupted or reduced to a therapeutically significant level. In one such an embodiment, the antibiotic is administered as sub-MIC (minimally inhibitive concentration) concentrations or doses. In one embodiment, the antibiotic is utilized and/or administered at a dose or concentration which serves to disrupt and/or permeabilise the cell wall and/or membrane, including so as to be inhibitory to the viability, growth or division of the bacteria, including as assessed by recognized and known bacterial sensitivity or growth and inhibition assays or methods. In one such embodiment, there is an independent therapeutic effect of each of the one or more antimicrobial agent(s) and a collective and combined therapeutic effect of the one or more antimicrobial agent and the one or more therapeutic molecule.

While the cell walls and surface structures of gram-positive and gram-negative bacteria are distinct, the cell wall structure can impede binding of antibodies in gram-negative bacteria. In gram-negative bacteria, for example, the ability of at least some anti-core and anti-lipid A antibodies to recognize corresponding epitopes on wild-type smooth lipopolysaccharide (LPS) or intact bacteria is restricted by the relative inaccessibility of such epitopes to antibody attack due to overlying O polysaccharide and core structures. The binding of HA-1A lipid-A reactive MAb to gram-negative bacteria exposed in vitro to inhibitory concentrations of antibiotics achieved in vivo in clinical practice has been evaluated (Seigel, S A et al (1993) Infect Immunol 61(2):512-519). The study was undertaken, in part, because HA-1A was being used in septic patients in conjunction with antibiotic therapy, and it was necessary to understand any immunochemical interactions between the two agents. In this study, overnight incubation of *E. coli* O111:B4 with inhibitory concentrations of caftazidime resulted in dose-dependent enhancement of HA-1A binding. Similar results were seen on exposure to other cell-wall active agents, including ceftriaxone, piperacillin, and imipenem. Antibody HA-1A binding was not enhanced, however, by exposure to gentamicin, which targets bacterial protein synthesis. Antibiotics which do not target the cell wall, including those with an intracellular target, did not enhance HA-1A antibody binding to the gram negative bacteria. In this study, alterations in bacterial cell morphology were observed with the antibiotic inhibitory concentrations utilized, and a reduction in average cell size and bacterial fragmentation was indicated by FACS analysis, as well as an increase in propidium iodide uptake and bacterial cell permeability.

Anti-Microbial Peptides

A wide range of antimicrobial peptides is secreted in plants and animals to challenge attack by foreign viruses, bacteria or fungi (Boman, H. G. (2003) J. Intern. Med. 254 (3):197-215). These form part of the innate immune response to infection, which is short term and fast acting relative to humoral immunity. These peptides are heterogeneous in length, sequence and structure, but most are small, cationic and amphipathic (Zasloff, M. (2002) Nature 415 (6870):389-395). Antimicrobial peptides have been considered as prospective antibiotics agents because their effect is rapid, broad spectrum and indifferent to resistance to standard antibiotics such as penicillins (Fischetti, V. A. (2003) Ann. N. Y. Acad. Sci. 987:207-214; Hancock, R. E. (1999) Drugs 57(4):469-473). Hundreds of such antimicrobial peptides have been studied extensively in order to understand the relationship between the structural features of the peptides and their antimicrobial activity, for the purpose of designing a new generation of antibiotics. Exemplary such known antimicrobial peptides are listed at an antimicorobial database (apps.unmc; Wang Z and Wang G (2004) NAR 32:D590-D592) and the content and disclosure of this site is incorporated herein by reference in its entirety. While the external cell wall may be the initial target, several lines of evidence suggest that antimicrobial peptides act by lysing bacterial membranes. Cells become permeable following exposure to peptides, and their membrane potential is correspondingly reduced. While the actual target and mode of action of antimicrobial peptides are incompletely understood, proposed models emphasize the need to coat or cover a significant part of the membrane in order to produce a lethal effect.

Protamines or polycationic amino acid peptides containing combinations of one or more recurring units of cationic amino acids, such as arginine (R), tryptophan (W), lysine (K), even synthetic polyarginine, polytryptophan, polylysine, have been shown to be capable of killing microbial cells. These peptides cross the plasma membrane to facilitate uptake of various biopolymers or small molecules (Mitchell D J et al (2002) J Peptide Res 56(5):318-325).

However, their success thus far has been limited, largely due to the requirement that they be present in a fairly high concentration to achieve killing. This high concentration exerts a potentially cytotoxic effect on human erythrocytes as well as other cells and tissues. For these reasons current applications of these peptides are mostly topical (Brown K. L. and Hancock R. E. W. (2006) Curr Opin Immunol 18:24-30).

The anti-microbial peptides find use in the present invention at lower doses, sub-effective-killing doses, as cell-wall or cell membrane disrupting agents. In addition, in combination with low dose antibiotics to act as (additional) disrupters, the peptides are more effective at lower doses, being more accessible to their target(s) in accordance with the invention, including in further combination with antibodies directed against cell membrane target(s), such as sortase.

Cell-Wall Degrading Enzymes

In an aspect, combinations of these basic/cationic proteins and/or other antimicrobial peptides with a cell-wall degrading enzyme. A cell-wall degrading enzyme is an enzyme which degrades components of the cell wall, including peptidoglycans, such as murein and pseudomurein, chitin, and teichoic acid. Cell-wall degrading enzymes can include, but are not limited to amidases, muramidases, endopeptidases, glucosaminidases. Examples of cell-wall degrading enzymes which are useful in compositions of the present invention include, but are not limited to endoglycosidases Type II, lysozymes and chitinases. Exemplary endoglycosidases Type II are disclosed in EP-A2-0 425 018.

Catalytic Antibodies

A catalytic antibody, also known as abzyme, is a large immunological protein that is naturally produced by the immune system and has the capability of catalyzing a chemical reaction similarly to enzymes. Ordinarily, antibody molecules simply bind; they do not catalyze reactions. Catalytic antibodies may be produced through immunization with a hapten molecule that is usually designed to resemble the transition state or intermediate of a desired reaction. These immunogen hapten molecules are specially designed to elicit antibodies that have binding pockets capable of catalyzing chemical reactions. For example, in the simplest cases, binding forces within the antibody binding pocket are enlisted to stabilize transition states and intermediates, thereby lowering a reaction's energy barrier and increasing its rate. This can occur when the antibodies have a binding site that is complementary to a transition state or intermediate structure in terms of both three-dimensional geometry and charge distribution. This complementarity leads to catalysis by encouraging the substrate to adopt a transition-state-like geometry and charge distribution. Not only is the energy barrier lowered for the desired reaction, but other geometries and charge distributions that would lead to unwanted products can be prevented, increasing reaction selectivity. In an alternative approach, anti-idiotype antibodies are utilized as the internal image of an enzyme active site for generating catalytic antibodies (Friboulet A et al (1994) Appl Biochem Biotechnol 47(2-3):229-237).

The important feature of catalysis by antibodies is that, unlike enzymes, a desired reaction selectivity can be programmed into the antibody by using an appropriately designed hapten. Catalytic antibodies almost always demonstrate a high degree of substrate selectivity. In addition, catalytic antibodies have been produced that have regioselectivity sufficient to produce a single product for a reaction in which other products are normally observed in the absence of the antibody. Finally, catalytic antibodies have been produced by immunization with a single-handed version (only left- or only right-handed) of a hapten, and only substrates with the same handedness can act as substrates for the resulting catalytic antibodies. The net result is that a high degree of stereoselectivity is observed in the antibody-catalyzed reaction. Catalytic antibodies have the advantage of high affinity for a pre-selected and specific chemical transformation with an efficiency adequate for medical applications Blackburn G B and Partridge L J (1996) Pure & Appl Chem 69(1 1):2009-2016; Wentworth P (2002) Science 296:2247-2249). Catalytic antibodies already provide alternative defensive enzymes, for example in selectively cleaving amyloid beta peptide or HIV gp120 coat protein (Paul S et al (2005) Springer Seminar Immunol 26(4):485-503).

Vancomycin targets and binds noncovalently to the L-Lys-D-Ala-D-Ala portion of cell-wall peptidoglycan substructures, inhibiting cross linking and leading to cell wall defects and bacterial lysis. In vancomycin-resistant *enterococci* (VRE) the predominant resistance strategy is replacement of pentapeptide D-Ala-D-Ala termini with D-Ala-D-Lac depsipeptide, resulting in a 1000 fold decrease in vancomycin affinity and blocking antibiotic activity. A catalytic monoclonal antibody, VCA33H3, has been generated that hydrolyzes the D-Ala-D-Lac depsipeptide in peptidoglycan precursors required for cell wall proteoglycan synthesis in VRE strains (Isomura S et al (2002) Bioorganic & Medicinal Chemistry Lett 12:861-864).

In an alternative or additional aspect of the invention, therapeutic molecules or modulating agents are sized to traverse or otherwise penetrate the cell wall to reach their target site or target protein or molecule.

The bacterial cell wall has a certain diffusability character, permitting diffusion of small molecules. Historical studies have estimated that monodisperse molecules can penetrate the cell wall if equivalently smaller than a glycol of $M_n$ (number-average molecular weight)=1,200 and res (Einstein-Stokes hydrodynamic radius)=1.1 nm (Scherrer R and Gerhardt P (1971) J Bact 107(3):7 18-735). Entry into and traversion through pores in the cell wall is an entirely different process than diffusion through the cell wall. Studies of the overall structure of the cell wall peptidoglycan fabric have assessed the penetration of fluorescein-labeled dextrans with a range of known molecular weights, to determine the effective cell wall pore size. The mean estimate of gram-positive *B. subtilis* pore hole radius is 2.12 nm (Demchick P and Koch A L (1996) J Bact 178(3):768-773). Koch and his investigators have determined that the size of a globular hydrophobic molecule, if it does not bind to wall components, that can pass freely through is roughly 25 kDa, and it is estimated that proteins of less than 50 kDa may possibly pass through the native cell wall under normal conditions. Dextrans of up to 70 kDa showed significant, measurable transit through the cell wall of *B. subtilis*. Thus, it is anticipated that therapeutic molecules of about 50 kDa, and up to about 70 kDa may pass through the cell wall of gram-positive bacteria to modulate cell membrane associated and/or embedded molecules.

Generation of, isolation or, or modification of therapeutic molecules, including antibodies, ligands, therapeutic peptides to sizes which are in the range of 50 kDa, even 70 kDa, including antibody fragments or antibody molecule components, portions of antibody chains, antibody domain molecules, antibody variable region molecules, may provide therapeutic, neutralizing, or modulating molecules with access to their bacterial cell membrane target proteins or molecules. An IgG molecule is approximately 150 kDa, while scFv is 25 kDa and Fab is 50 kDa.

Camelid and Domain Antibodies

Attempts have been made to reduce the size of the minimum antibody fragment required for antigen binding and alternatives are emerging for antibody molecules with reduced size or segments, while maintaining specificity and activity. While scientific dogma held that antigen recognition and binding depend on the presence of domains in both the heavy and light chains, it has been shown that single domains are sufficient to ensure specific binding, if at a somewhat reduced affinity. Single chain antibody molecules can be recombinantly generated to possess only single heavy chain domains (Ward E S et al (1989) Nature 341:484-5; Dick H M (1999) BMJ 300:959-960). These domain antibodies (dAbs) correspond to the variable region of either the heavy $V_H$ or the light $V_L$ chains of human antibodies. Camels (Camelidae) naturally possess functional heavy chain antibodies devoid of light chains. In camelized antibodies ($cV_H$) a modified human $V_H$ domain is obtained through mimicking camel heavy chains for use as a small recognition unit (Davis J and Reichman L (1994) Febs Lett 339:285-290; Davis J and Reichman L (1996) Prot Engin 9:531-537). The variable domains of camel antibodies reflect the absence of a $V_L$ partner often having longer CDR3s and folding back on the VH surface. Camelized human single domain antibody libraries have been generated for isolation and screening (Tanha J et al (2001) J Biol Chem 276(27):24774-24780).

Compositions

The cell wall and/or cell membrane disrupters and the target modifying agents, modulating agents or binding agents, may be prepared in pharmaceutical compositions, with a suitable and acceptable carrier and at a strength effective for administration by various means to a patient experiencing an adverse medical condition associated with bacterial infection or exposure to resistant bacteria or the specific need for the treatment thereof. The compositions may comprise one or more disrupter, alone or in combination with, one or more target modifying, modulating or binding agent. A variety of administrative techniques may be utilized, among them topical, enteral, and parenteral techniques. Administration may be via any suitable mode or method, such as oral, rectal, transmucosal, transdermal, subcutaneous, intravenous and intraperitoneal injections, catheterizations and the like. Average quantities of the disrupters and/or agents may vary and in particular should be based upon the recommendations and prescription of a qualified physician or veterinarian.

The disrupters and/or agents of the present invention will usually be administered in the form of a pharmaceutical composition, which may comprise at least one component in addition to the disrupters and/or agents. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at an infection site.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. For intravenous, injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection; or Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the target agent, particularly antibody or fragment thereof, herein described and the disrupter, and may further or additionally comprise other agents, hormones, anti-mitotic agents, or immune modulators. Other treatments or therapeutics may include the administration of suitable doses of pain relief drugs such as non-steroidal anti-inflammatory drugs (e.g. aspirin, paracetamol, ibuprofen or ketoprofen) or opiates such as morphine, or anti-emetics. In addition, the composition may be administered with hormones such as dexamethasone, immune modulators, such as interleukins, tumor necrosis factor (TNF) or other growth factors, colony stimulating factors, or cytokines which stimulate the immune response and reduction or elimination of infectious agents or bacterial cells. The composition may also be administered with, or may include combinations along with other anti-bacterial antibodies.

The present invention further contemplates therapeutic compositions useful in practicing the therapeutic methods of this invention. A subject therapeutic composition includes, in admixture, a pharmaceutically acceptable excipient (carrier) and one or more of a disrupter and/or modifying, modulating or binding agent, including an antibody or fragment thereof, as described herein as an active ingredient. The preparation of therapeutic compositions which contain polypeptides, analogs or active fragments as active ingredients is well understood in the art. Typically, antibody or immunoglobulin compositions are prepared as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A polypeptide, analog or active fragment can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The therapeutic disrupter and/or modifying, modulating or binding agent-containing compositions are conventionally administered intravenously, as by injection of a unit dose, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of inhibition or neutralization desired. Precise amounts of active ingredient required to be administered depend on the judgment of the practitioner and are peculiar to each individual. Suitable dosages may be in the range of milligrams, micrograms, or nanograms of active ingredient per kilogram body weight of individual per day and depend on the route of administration and the type of agent or active ingredient in a composition. Suitable regimes for initial administration and further or continued administration are also variable, but are typified by an initial administration followed by repeated doses at one or more time (e.g., day(s), hour(s) or minute(s)) intervals by a subsequent injection or other administration. Alternatively, continuous intravenous infusion sufficient to maintain sufficient, appropriate, or effective concentrations in the blood or at the site of infection or compromise are contemplated.

It is further intended that analogs may be prepared from nucleotide sequences of the protein complex/subunit derived within the scope of the present invention. Analogs, such as fragments, may be produced, for example, by pepsin digestion of material. Other analogs, such as muteins, can be produced by standard site-directed mutagenesis of coding sequences. Analogs exhibiting "disrupter activity" and/or "cell wall or cell membrane target modifying, modulating or binding activity", whether functioning as promoters or inhibitors, may be identified by known in vivo and/or in vitro assays.

In accordance with the above, an assay system for screening potential agents effective as disrupters, or molecules capable of modifying, modulating or binding to cell wall and/or cell membrane targets in gram positive bacteria may be prepared. The bacterial cells and their target(s) may be introduced into a test system, and the prospective agents or molecules may also be introduced into the resulting cell culture, and the culture thereafter examined to observe any changes in the activity of the cells, or the cell wall and/or cell membrane targets, due either to the addition of the prospective agent or molecules alone, or due to the effect of added quantities of the agent(s) and modulator(s).

The labels most commonly employed for these studies are radioactive elements, enzymes, chemicals which fluoresce when exposed to ultraviolet light, and others. A number of fluorescent materials are known and can be utilized as labels. These include, for example, fluorescein, rhodamine, auramine, Texas Red, AMCA blue, Alexa Fluor®, Green fluorescent protein (GFP), fluorescent proteins of other colors, and Lucifer Yellow. A particular detecting material is anti-rabbit antibody prepared in goats and conjugated with fluorescein through an isothiocyanate. The radioactive label can be detected by any of the currently available counting procedures. The preferred isotope may be selected from $^3$H, $^{14}$C, $^{32}$P, $^{35}$S, $^{36}$Cl, $^{51}$Cr, $^{57}$Co, $^{58}$Co, $^{59}$Fe, $^{90}$Y, $^{125}$I, $^{131}$I, and $^{186}$Re.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090; 3,850,752; and 4,016,043 are referred to by way of example for their disclosure of alternate labeling material and methods.

The invention may be better understood by reference to the following non-limiting Example, which is provided as exemplary of the invention. The following example is presented in order to more fully illustrate the invention and embodiment(s) and should in no way be construed, however, as limiting the broad scope of the invention.

EXAMPLE 1

General Approach

Evaluation of cell wall and/or membrane permeability modulators and/or the effects of antibody or other therapeutic macromolecules in various combinations, at various concentrations is conducted using standard and recognized methods in the art. Bacterial cells are grown to appropriate confluence or cell density and combined with agents (antibiotics, antimicrobial peptides) and/or antibodies or macromolecules (such as sortase antibody(ies)). The effect of these combinations on cell growth is determined. The effect effects of these combinations on sortase, PBP, ABC transporter, β-lactamase, pore protein, or other target activity is determined. In the instance of a sortase target, the effect of these combinations on surface proteins, such as Protein A, is evaluated. The effect of these combinations on bacterial virulence and/or infection is assessed.

Bacterial strain(s) are grown in appropriate media. *S. aureus* strains, such as RN4220, Newman, and/or N315, are grown in tryptic soy broth (TSB) at 37° C. *S. pneumoniae* strains, such as TIGR4, are grown at 37° C. in Todd-Hewitt broth with 0.5% yeast extract (THY) or on blood agar plates.

Protein A may be stained on cells and/or immunoprecipitated from cells using IgG, including Cy3-conjugated goat anti-rabbit IgG (Invitrogen) (1:1000), fluorescein isothiocyanate (FITC)-IgG (Invitrogen) (1:25), and Alexa Fluor 647-IgG (Invitrogen) (1:50 or 1:250 dilution) (DeDent A C et al (2007) J Bact 189(12):4473-4484).

Immunoblotting for bacterial proteins, including cell wall or surface proteins, may be conducted by isolating total cell (lysate) and cell wall (supernatant) fractions after incubation with lysostaphin (buffer with 0.1 mg/ml) and centrifugation at 8,000×g for 3 minutes, and precipitating the proteins with 7.5% trichloroacetic acid. Protein sediment is suspended in loading buffer and subjected to SDS-PAGE, followed by immunoblot analysis with monoclonal antibody SPA-27 (Sigma; anti-protein A antibody) or polyclonal antibody raised against either SrtA or L6 (cytoplasmic protein) (DeDent A C et al (2007) J Bact 189(12):4473-4484).

Animal infectivity and animal infections are assessed using various methods. Intravenous *S. pneumoniae* infection and virulence of pneumococci is examined in 6-12 week old female CBA/CaHN-Btk$^{rid}$/J mice (Jackson Laboratories, Bar Harbor, Me.) using a systemic model of infection (Ren B et al (2003) Infect Immunol 7 1:75-85). Mice are injected with 300 to 1,000 CFU diluted in Ringer's solution and survival time is monitored.

*Staphylococcal* infection may be monitored in vivo by inoculating 6-8 week old C57BL/6 or Swiss-Webster mice with *staphylococcal* suspension into the tail vein. Five days after infection, mice are euthanized with $CO_2$. Kidneys are excised, weighed, homogenized in 0.5% Triton X-100, and *staphylococci* counted by dilution and colony formation (Mazmanian S K et al (2000) PNAS 97(10):55 10-55 15).

Rodent models of nasal colonization by *S. aureus* are utilized (Schaffer A C et al (2006) Infect Immunol 74(4): 2145-2153; Kiser K B et al (1999) Infect Immunol 67:5001-5006). A nasopharyngeal colonization model in adult mice may be used with *S. pneumoniae* (Wu H Y et al (1997) Micob Pathog 23:127-137).

Sortase activity may also be assessed in vivo by following maturation of pulse-labeled surface proteins, for example using the Scb-Spacws reporter (Ton-That H and Schneewind O (1999) JBC 274:243 16-24320).

EXAMPLE 2

Sortase

Reaction of Sortase-specific Antibodies with
*Staphylococcus aureus* Grown in the Presence of
Sub MIC Antibiotics In these experiments we assessed whether the cell wall of *Staphylococcus aureus* grown in the presence of sub-MIC of antibiotics will allow sortase-specific polyclonal and monoclonal antibodies to interact directly with the sortase on the bacterial cell membrane on live and growing bacterial cells.

Previously reported studies used low-dose treatment of paraformaldehyde/glutaraldehyde fixed *Streptococcus pyogenes* cells with the phage lysin PlyC, specific for the cell wall of *S. pyogenes*, to permeabilize the cell wall to anti-sortase antibodies (Raz A and Fischetti V (2008) PNAS 105(47): 18549-18554). In these earlier experiments, in addition to fixing the cells, the addition of methanol was required to equalize the cellular and environmental osmotic pressure and prevent membrane bulging through the PlyC-generated holes in the cell wall.

Figure 3A:
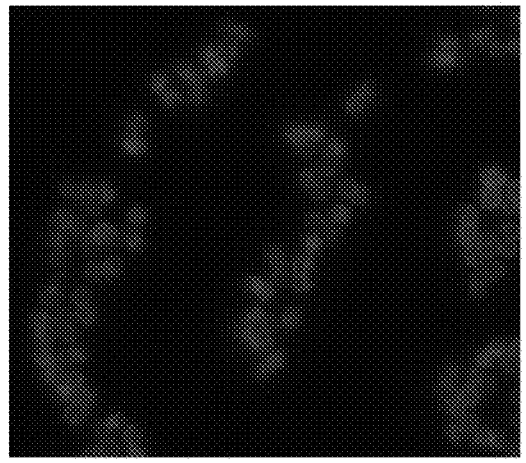
FIGS. 3A and 3B depicts sortase distribution in protein A mutant *S. aureus* after permeabilization by lysostaphin. *S. aureus* cells were grown to OD600 0.5 in media and fixed immediately. The cells were permeabilized by lysostaphin, stained for anti-mouse sortase (red), and subsequently labeled for cell wall using WGA488-F1TC conjugated (green) and for DNA using DAPI (blue).
Figure 3B:
Figure 4A:
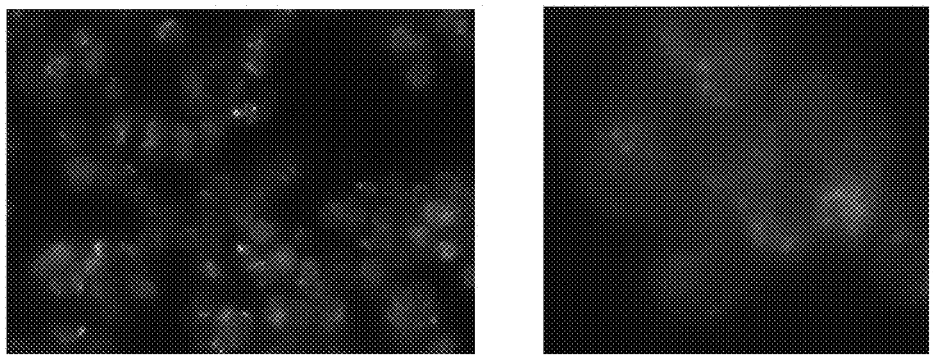
FIG. 4A-4C depicts sortase distribution in protein A mutant *S. aureus* after antibiotic treatment. *S. aureus* cells were grown to OD$_{600}$ 0.5 in media with penicillin (A), ampicillin (B), or without any antibiotics (C). The cells were stained with polyclonal anti-rabbit sortase (green), and subsequently labeled for cell wall using WGA594-F1TC conjugated (red) and for DNA using DAPI (blue). The right panel is a 4× enlargement of the left panel in A, B, and C.
Figure 4B:
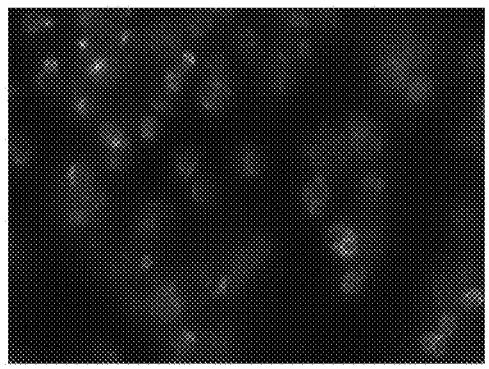
Figure 4B:
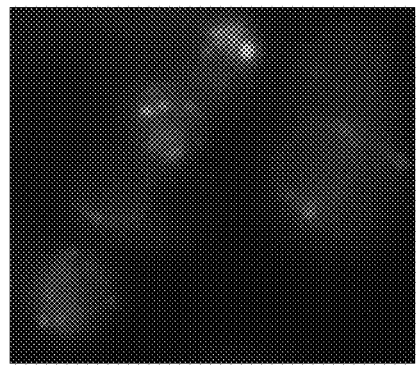
Figure 4C:
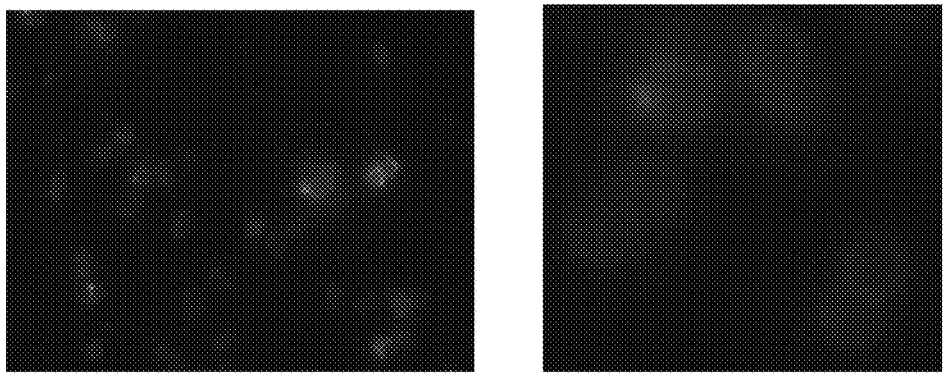

In the present experiments, *Staphylococcus aureus* was treated with low doses of the *staphylococcus*-specific phage lysin, lysostaphin, and monoclonal antibody generated against *S. aureus* sortase was shown to reach and recognize sortase in cells at the cell membrane by immunoflourescence. FIGS. 3A and 3B shows sortase distribution in protein A mutant *S. aureus* after permeabilization by lysostaphin. *S. aureus* cells were grown to $OD_{600}$ 0.5 in media and fixed immediately. The cells were permeabilized by lysostaphin, stained for anti-mouse sortase antibody (red), and subsequently labeled for cell wall using WGA488-FITC conjugated (green) and for DNA using DAPI (blue).

The MIC dose of two cell wall affecting antibiotics, ampicillin and penicillin, was detrmined for the protein A negative *S. aureus* strain 8325-4. We found that on growing the *staphylococci* in the presence of sub-MIC of antibiotics such as ampicillin and penicillin, the bacteria were able to grow similar to control bacteria without antibiotic. The addition of anti-sortase antibodies and flourescein-labeled goat anti-rabbit antibodies resulted in florescence patterns expected of sortase on the membrane surface. These results are depicted in FIG. 4, demonstrating that addition of antibiotics to bacteria, even at sub-MIC doses which do not affect cell growth, permits entry of cell membrane protein targeted anti-sortase antibodies, at an amount sufficient for immunofluorescence. In the absence of antibiotic, no anti-sortase antibody signal is seen by immunofluorescence, indicating that sufficient antibody for signaling does not reach the sortase at the cell membrane.

Figure 5:
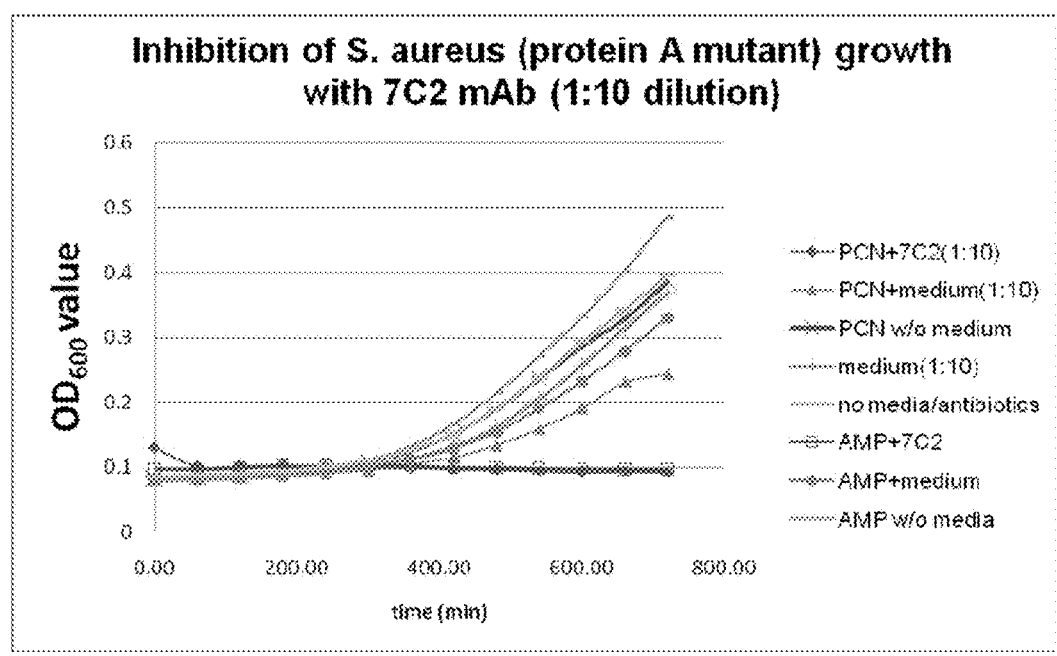
FIG. 5 depicts growth of protein A mutant *S. aureus* in the presence of antibiotics at sub-MIC doses, with and without antibody directed against sortase. The figure graphs the results of *S. aureus* cells grown in the presence of sub MIC of ampicillin, penicillin with or without mouse anti-sortase monoclonal antibody 7C2 at a dilution of 1:10. PCN: Penicillin, AMP: Ampicillin, Medium: tissue culture medium, w/o medium: BHI alone.

In a separate set of experiments, we assessed the effect of anti-sortase antibodies, in the presence and absence of antibiotic, on the growth of the *staphylococci*. Monoclonal supernatants were used for these experiments and tissue culture media used as controls. We found that when *staphylococci* were grown in the presence of sub MIC of antibiotics, no significant inhibition of growth was seen even in the presence of tissue culture media. However, when monoclonal antibodies were added at either 1:10 or 1:100 dilution, inhibition of growth was observed in both cases. Exemplary growth curve results with monoclonal antibody 7C2 at 1:10 dilution are depicted in FIG. 5. The growth results are tabulated in TABLE 3 below based on final OD readings of multiple growth experiments. In each instance, significant growth inhibition is observed with a combination of sub-MIC antibiotics and anti-sortase antibody.

TABLE 3

GROWTH OF MRSA WITH ANTIBIOTIC AND SORTASE ANTIBODY

|  | Final OD Reading 1 | Final OD Reading 2 | Average OD | P value (antibiotics + Ab vs antibiotics + medium) |
|---|---|---|---|---|
| 2H11Ab 1:10 | | | | |
| PCN + Ab | 0.0892 | 0.1021 | 0.09565 | 0.0161 |
| PCN + medium | 0.218 | 0.2712 | 0.2446 | |
| 2H11 Ab 1:100 | | | | |
| PCN + Ab | 0.2631 | 0.1694 | 0.21625 | 0.0499 |
| PCN + medium | 0.3508 | 0.3561 | 0.35345 | |
| 2H11 Ab 1:10 | | | | |
| AMP + Ab | 0.0972 | 0.1027 | 0.09995 | 0.0102 |
| AMP + medium | 0.2975 | 0.3641 | 0.3308 | |
| 2H1 Ab 1:100 | | | | |
| AMP + Ab | 0.2999 | 0.1847 | 0.2423 | 0.0411 |
| AMP + medium | 0.4216 | 0.4627 | 0.44215 | |
| 7C2 Ab 1:10 | | | | |
| PCN + Ab | 0.0877 | 0.0969 | 0.0923 | 0.0150 |
| PNC + medium | 0.218 | 0.2712 | 0.2446 | |
| 7C2 Ab 1:100 | | | | |
| PCN + Ab | 0.1783 | 0.2048 | 0.19155 | 0.0034 |
| PNC + medium | 0.3508 | 0.3561 | 0.35345 | |
| 7C2 Ab 1:10 | | | | |
| AMP + Ab | 0.0928 | 0.1004 | 0.0966 | 0.0099 |
| AMP + medium | 0.2975 | 0.3641 | 0.3308 | |
| 7C2 Ab 1:100 | | | | |
| AMP + Ab | 0.2723 | 0.294 | 0.28315 | 0.0103 |
| AMP + medium | 0.4216 | 0.4627 | 0.44215 | |

Materials and Methods

Bacteria Strain and Culture Conditions: Protein A negative *Staphylococcus aureus* derived from strain 8325-4 was grown to $OD_{600}$ 0.5 in Brain-Heart Infusion medium at 37° C. (Patel A H et al (1987) Infect Immun 55(12):3 103-3 110). When applicable, antibiotics were added to the media at sub-MIC doses.

Reagents and Antibodies:

Sortase monoclonal antibodies. *Staphylococcal* sortase monoclonal antibodies were prepared by cloning the *staphylococcal* sortase in an expression vector and purifying it by ion exchange chromatography. Purified sortase was emulsified in complete Freund's adjuvant and used to immunize mice with 200 ug/mouse intradermally. One month later the mice were boosted by the same route with 100 ug/mouse in incomplete Freund's adjuvant. After 2 more monthly boosts, the animals were bled to determine the antibody titer and the animals were sacrificed and spleen used to produce monoclonal antibodies. Antibody-producing cells were screened for reactivity to *staphylococcal* sortase by ELISA and cells producing antibodies with the highest reactivity were further processed to produce a monoclonal. Two initial anti-*S. aureus* sortase antibodies designated SrtAb1 and SrtAb2 were used in the present studies.

Cloning of *Staphylococcal* srtA. The DNA sequence encoding the *S. aureus* srtA gene, lacking its N-terminal transmembrane domain (amino acids 1-25), was amplified from the genomic DNA of strain MW2 (community acquired MRSA), using primers (SEQ ID NO: 2)
5_SA_srtA_SalI
(5-CCCGTCGACAAACCACATATCGATAATTATCTTCACG-3)

and

3_SA_srtA_NotI
(5-GGGGCGGCCGCTTATTTGACTTCTGTAGCTACAAAGATTTTAC-3).

The resulting PCR product was inserted into the SalI and NotI restriction sites of a modified pET21a plasmid (obtained from Dr Erec Stebbins, Rockefeller University) yielding pAR203. The nucleotide sequence of vector pAR203 is provided in FIG. 6 (SEQ ID NO: 7). This plasmid contains an open reading frame, in which a hexahistidine tag followed by a 3C protease cleavage site, are fused to the N-terminus of the soluble portion of SrtA.

Purification of sortase. An overnight culture of *E. coli* BL21/pAR203 was diluted 1:100 into 2 L of LB medium containing ampicillin and grown at 37 C with shaking. Upon reaching $OD_{600}$ 0.6, the expression of H6-3C-SrtA was induced with ImM IPTG for 6 hours at room temperature. The cells were harvested and resuspended in 100 ml MCAC buffer (30 mM Tris pH 7.4, 0.5 M NaCl, 10% glycerol, 1 mM DTT), and homogenized. Cell debris was removed by centrifugation, and the supernatant was filtered through a 0.22-μm filter (Millipore). The cleared lysate was loaded on a NiNTA column equilibrated with MCAC buffer, followed by washes with MCAC containing 5 mM imidazole and gradual elution with MCAC containing 50 mM imidazole and 100 mM imidazole. The initial elution fractions containing the bulk of the protein were kept separately, while the later elution fractions, containing cleaner material, were concentrated using an amicon ultrafiltration device fitted with a 3-kDa molecular weight cutoff membrane to a final concentration of 2.3 mg/ml and used for mouse immunization.

The sequence of the srtA fusion protein: (the amino acids fused to the N-terminus of the soluble portion of srtA are italicized and bolded):

(SEQ ID NO: 3)
MASMTGGQQMGRGSNVQGHLPLVPR

GSKLHHHHHHLEVLFQGPVDKPHIONYLH

DKDKDEKIEQYDKNVKEQASKDKKQQAKPQIPKDKSKVAGYIEIPDADIK

EPVYPGPATPEQLNRGVSFAEENESLDDQNISIAGHTFIDRPNYQFTNLK

AAKKGSMVYFKVGNETRKYKMTS1RDVKPTDVEVLDEQKGKDKQLTLITC

DDYNEKTGVWEKRKIFVATEVK*

Antibodies. Anti-rabbit polyclonal sortase antibody (Abeam, Corp., ab 13959) was used at a concentration of 0.05 mg/ml. Affinity-purified mouse anti-sortase A antibody (generated as described above) was used at 1:3 for immunofluorescence. Goat anti-mouse IgG, Rhodamine Red (Jackson ImmunoResearch) was used at 1:500. Goat anti-rabbit IgG, FITC conjugate (Sigma) was used at 1:100. WGA Alexfluor 488 and 594 conjugate (Invitrogen) were used at 5 µg/ml and pseudocolored green. DAPI (Sigma) was used at 1 µg/ml.

Ampicillin and Penicillin MIC. Serial 2-fold dilutions of penicillin and ampicillin were prepared in a microtiter plate. Overnight culture of *Staphylococci* were diluted 1:100 in BH1 media and 100 ul was added to each well and the plate incubated for 12 h. Wells without antibiotic served as controls. The highest dilution of antibiotic showing normal growth was used for further experiments. Ampicillin at 0.1 ug/ml and Penicillin at 0.02 ug/ml were used in these experiments.

Antibiotic Experiments:

To determine if the mouse anti-sortase antibodies with and without antibiotics had an effect on bacterial growth, *S. aureus* was grown in 96-well plate at 37° C. for 12 hours in the presence of ampicillin (0.1 ug/ml) or penicillin (0.02 ug/ml). Mouse anti-sortase monoclonals were added to each cell-antibiotic culture at a dilution of either 1:10 or 1:100. $OD_{000}$ values were measured every 5 mins for 12 hours in a 96-well spectrophotometer.

Immunostaining:

Phosphate buffer (pH 7.4) and paraformaldehyde were added to the cell culture medium to final concentrations of 30 mM and 2.6%, respectively. The mixture was incubated for 15 min at room temperature, then 30 min on ice. The cells were then centrifuged, washed once in PBS and resuspended in PBS. The resuspended cells were attached to poly-L-lysine coated coverslips. If not grown in antibiotics medium, the cells were permeabilized with cold methanol, and treated with lysostaphin (20 µg/ml, Sigma) in PBS. Cells were then blocked with goat serum supplemented with 1% gelatin from cold-water fish skin for 10 mins at room temperature. Primary and secondary antibodies and dyes were diluted in PBS containing 2% BSA and 1% gelatin, and incubated with the cells in a moist chamber for 1 hour at room temperature (secondary incubation in the dark). Between incubation steps, the cells were washed thoroughly with PBS. To reduce bleaching of the fluorochromes, the cover slips were mounted in 50% glycerol and 0.1% I-7-phenylenediamine in PBS (pH 8) and sealed with nail polish.

EXAMPLE 3

In Vivo Studies

Measuring in vivo activity. *S. aureus* strain (MRSA) is grown to log-phase, centrifuged and resuspended to a predefined titer of about $10^{10}$ cfu/ml. For intranasal infection, 6-wk-old female C57BL/6J, outbred Swiss or BALB/c mice (weight range 22 to 24 g, Charles River Laboratories, Wilmington, Mass.) are anesthetized with a mixture of ketamine (Fort Dodge Animal Health, Fort Dodge, Iowa, 1.2 mg/animal) and xylazine (Miles Inc., Shawnee Mission, Kans., 0.25 mg/animal), and inoculated with 15 ml of the bacterial suspension per nostril (n=10). The animals are divided into treatment groups and administered various concentrations of antibiotic or antibody, alone or in combination, or sterile saline intraperitoneal six hours after infection and every six hours thereafter for 3 days. The survival rate for each group is observed up to 7 days post infection.

In Vivo Nasal Decolonization of MRSA. Carriage of both MSSA and MRSA in the human anterior nares is the major reservoir for *S. aureus* infection. Studies have shown that roughly 80% of the population could be nasally colonized by *S. aureus*, and that colonization can be an increased risk factor for developing other more serious *S. aureus* infections (Kluytmans, J., A. van Belkum (1997) Clin Microbiol Rev 10(3):505-520). In fact, assessment of nasal colonization is being instituted on admission to critical care settings in hospitals in the U.S. Elimination of nasal carriage in the community or in the hospital setting thus could possibly reduce the risk of infection and slow the spread of drug resistant *S. aureus*. To study the ability of sub-MIC antibiotics in combination with cell membrane targeted antibodies (anti-sortase antibodies) to reduce MRSA colonization of the nasal mucosa, C57BL/6J mice are intranasally inoculated with ~2×10$^7$ of a spontaneously streptomycin resistant strain of MRSA (191-SMR). Twenty-four hours post-infection mice are administered three doses hourly of either phosphate buffered saline (control), antibody, or antibody and antibiotic into the nasal passages. One hour after the last treatment, mice are sacrificed and bacteria colonies enumerated on Spectra MRSA agar (a selective chromogenic medium developed to diagnostically detect MRSA nasal colonization) and Columbia blood agar. Three independent experiments are performed to evaluate at least 10 mice for each treatment group. Significantly reduction in the mean CFU on the nasal mucosa on treatment with antibiotic and antibody is determined.

Treatment of Systemic MRSA Infections. In order to assess whether combination sub-MIC antibiotic and anti-cell membrane target antibody (anti-sortase antibody) treatment can prevent death resulting from systemic MRSA infections, 4 week old FVB/NJ mice are intraperitonally injected with ~5×10$^5$ CFU of the community-acquired MRSA strain MW2 in 5% mucin (preliminary experiments determined that 5×10$^5$ CFU was 10× the LD$_{100}$ dose for a twenty-four hour period). Within 3 hours of IP injection the MRSA infection is systemic, i.e., MRSA are recovered in high numbers from heart, liver, spleen, and kidney. Treatment occurs three hours post-infection, with either 20 mM phosphate buffer alone or antibiotic with or without antibody in 20 mM phosphate buffer injected IP (intraperitoneally). Mice are monitored for survival over ten days. The results from independent experiments are combined and the mice survival data plotted with a Kaplan Meier Survival curve. Positive results are seen wherein within twenty-four hours all of the control mice die of bacterial sepsis, while only some or none of the treated mice die, and remaining treated mice survive over the course of the experiments.

EXAMPLE 4

Penicillin Binding Proteins

Penicillin binding proteins (PBPs) are membrane-bound enzymes that catalyze carboxypeptidase or transpeptidase reactions for bacterial peptidoglycan synthesis. Bacteria have multiple PBPs. In methicillin-susceptible *Staphylococcus aureus* (MSSA), four PBPs (PBP1, 85 kDa; PBP2, 81 kDa; PBP3, 75 kDa; and PBP4, 45 kDa) have been identified, and PBP2' (A) is also found in methicillin-resistant *S. aureus* (MRSA). *S. aureus* PBP1-4 are targets of β-lactam antibiotics. β-lactam antibiotics bind to these PBPs due to structural similarity, and cell wall synthesis is inhibited. In MRSA, PBP2' (A) has low affinity for β-lactam antibiotics, so this PBP can still function in the presence of a concentration of β-lactam antibiotics that inhibits other PBPs.

Antibodies directed to *S. aureus* PBP2a available from Calbioreagents are used to assess antibody targeting to PBP2a in live bacteria cultures:

| Specificity | Ab Name | Ab type | Bacterial Protein Target | Ab Species |
|---|---|---|---|---|
| PBP2a | 6G10 | Monoclonal | Penicillin Binding Protein 2a (MRSA) | Mouse |
| PBP2a | 19B1 | Monoclonal | Penicillin Binding Protein 2a (MRSA) | Mouse |
| PBP2a | 17A10 | Monoclonal | Penicillin Binding Protein 2a (MRSA) | Mouse |
| PBP2a | 17C8 | Monoclonal | Penicillin Binding Protein 2a (MRSA) | Mouse |
| PBP2a | 8A5 | Monoclonal | Penicillin Binding Protein 2a (MRSA) | Mouse |
| PBP2a | 9C6 | Monoclonal | Penicillin Binding Protein 2a (MRSA) | Mouse |

Various similar anti-PBP2a antibodies, directed against PBP2a of MRSA strain, are commercially available including from Fitzgerald Industries International and MyBiosource, including antibody M8 121 52 1, M8 121522 and M8 12 1523. Additional PBP2a antibodies are described and utilized including Komatsuzawa et al which describes cloning and characterization of the gene pbpF encoding a penicillin-binding protein, PBP2B, in *Staphylococcus aureus*. (Komatsuzawa H et al Antimicrobial Agents and Chemotherapy (1999) 43(7): 1578-1583) and utilize an antibody specific to *S. aureus* PBP2a, as well as Zhou et al (Zhou Y et al., Bacteriol 190:2 (2008), p. 508-514).

Antibodies directed against other gram positive PBPs have been described and are known and are suitable in combinations with antibiotics in accordance with the invention for more effective targeting to and activity against PBPs in live and growing gram positive bacterial cultures and model systems. Tomasz and colleagues have described penicillin-binding proteins or penicillin-susceptible and penicillin-resistant pneumococci and assessed immunological relatedness of the PBPs in these strains using antibodies generated against PBP1a, PBP2b and PBP3 (Hakenbeck R et al (1986) Antimicrob Agents and Chemother 30(4):553-558). Signoretto teach anti-PBP5 antibody against *enterococci* (Signoretto C et al., FEMS Lett 123:1-2 (1994), p 99-106). Morlot et al generated and report studies using *S. pneumoniae* specific anti-PBP1a, 1b, 2a polyclonal antisera to assess PBP localization and, combined with genetic experiments, determine the essential role of PBPs in cell wall synthesis and cell division (Morlot C et al (2003) Mol Microbiol 50(3) 845-855). In order to carry out these immunofluorescence studies, Morlot raised rabbit antisera against the recombinantly produced extracellular domains of the five high molecular weight PBPs from *S. pneumoniae*.

To assess antibody and antibiotic effects in bacteria, a suitable bacterial strain expressing antibody-directed protein is grown with antibody alone or in combination with antibiotic(s). For *S. aureus*, protein A negative *Staphylococcus aureus* derived from strain 8325-4 (or such other suitable *S. aureus* strain) is grown to $Oo_{600}$ 0.5 in Brain-Heart Infusion medium at 37° C. When applicable, antibiotics are added to the media at low doses, particularly sub-MIC doses. MIC doses are determined by serial 2-fold dilutions of antibiotic (s) prepared in microtiter plates. Overnight culture of *Staphylococci* are diluted 1:100 in BHI media, 100 ul added to each well and the plate incubated for 12 h. Wells without antibiotic serve as controls. The highest dilution of antibiotic showing normal growth is used for further experiments. Antibiotics are selected from cell wall synthesis, peptidoglycan altering, and DNA and protein synthesis inhibitor classes as described above, and tested for immunofluorescence, cell growth effects and in vivo effects as described above and hereinbelow. An exemplary results table is depicted below.

| Antibiotic | Antibody Target | Immunofluor | Cell Growth Effect | In Vivo Effect |
|---|---|---|---|---|
| Glycopeptide | None | − | − | − |
|  | PBP | + | + | + |
|  | Other | + | + | + |
| Penicillin | None | − | − | − |
|  | PBP | + | + | + |
|  | Other | + | + | + |
| Cephalosporin | None |  |  |  |
|  | PBP |  |  |  |
| Polypeptide/ Lipopolypeptide | None |  |  |  |
|  | PBP |  |  |  |
|  | Other |  |  |  |
| Carbapanem | None |  |  |  |
|  | PBP |  |  |  |
|  | Other |  |  |  |
| Quinolone | None |  |  |  |
|  | PBP |  |  |  |
|  | Other |  |  |  |
| Macrolide | None |  |  |  |
|  | PBP |  |  |  |
|  | Other |  |  |  |
| Sulfonamide | None |  |  |  |
|  | PBP |  |  |  |
|  | Other |  |  |  |
| Aminoglycoside | None |  |  |  |
|  | PBP |  |  |  |
|  | Other |  |  |  |

Antibiotic experiments: To determine if the antibodies with and without antibiotics have an effect on bacterial growth, bacteria (*S. aureus, S. pneumoniae, enterococci,* etc.) are grown in 96-well plates at 37° C. for 12 hours in the presence of the antibiotic(s). Antibodies are added to each cell-antibiotic culture at appropriate dilution and cell growth (e.g. by $OD_{600}$ values) is measured (for instance, every 5 mins for 12 hours in a 96-well spectrophotometer).

EXAMPLE 5

ABC Transporters

ABC transporters are essential for cell viability, virulence, and pathogenicity. In bacterial systems, ABC transporters mediate extrusion of surface components of the bacterial cell (e.g. capsular polysaccharides, lipopolysaccharides, and teichoic acid), proteins involved in bacterial pathogenesis (e.g. hemolysis, heme-binding protein, and alkaline protease), heme, hydrolytic enzymes, S-layer proteins, competence factors, toxins, lantibiotics, bacteriocins, peptide antibiotics, drugs and siderophores. They also play important roles in biosynthetic pathways, including extracellular polysaccharide biosynthesis and cytochrome biogenesis. The ABC transporter Ecs of *Staphylococcus aureus* has been shown to be essential for *staphylococcal* virulence using genetic inactivation of the escAB operon (Johnsson I-M et al (2010) PLoSOne 5(12):e14209. Doi:10.137 1/jpournal-.pone.0014209). The Ecs transport function was shown to be essential for normal structure and function of the cell wall and Esc mutants had higher susceptibility to ribosomal antibiotics and plant alkaloids chelerythrine and sanguinarine. Antibodies against various bacterial ABC transporters have been described and are known. Bates et al have described and used antisera specific to Sia (*streptococcus* iron acquisition) transporter in *Streptococci* (Bates C S et al. Infection and Immunity 7 1:3 (2003), 1042-1055). Antisera to *staphylococcal* ABC transporter Vga(A) has been described (Chesneau O et al., Antimicrob Agents Chemother 49:3 (2005), 973-980). Burnie et al describe generation of an antibody to Vancomycin-resistant *enterococci* ABC1 that conferred resistance to infection in mice (Burnie J et al, FEMS Immunology and Medical Microbiol 33:3 (2002), 179-189).

To assess antibody and antibiotic effects in bacteria, a suitable bacterial strain expressing antibody-directed protein is grown with antibody alone or in combination with antibiotic(s). For *S. aureus*, protein A negative *Staphylococcus aureus* derived from strain 8325-4 (or such other suitable *S. aureus* strain) is grown to $OD_{600}$ 0.5 in Brain-Heart Infusion medium at 37° C. When applicable, antibiotics are added to the media at sub-MIC doses. MIC doses are determined by serial 2-fold dilutions of antibiotic(s) prepared in microtiter plates. Overnight culture of *Staphylococci* were diluted 1:100 in BHI media and 100 ul was added to each well and the plate incubated for 12 h. Wells without antibiotic serve as controls. The highest dilution of antibiotic showing normal growth is used for further experiments. Antibiotics are selected from cell wall synthesis, peptidoglycan altering, and DNA and protein synthesis inhibitor classes as described above, and tested for immunofluorescence, cell growth effects and in vivo effects as described and depicted above and herein.

Antibiotic experiments: To determine if the antibodies with and without antibiotics have an effect on bacterial growth, bacteria *S. aureus, Streptococci, enterococci*, etc.) is grown in 96-well plates at 37° C. for 12 hours in the presence of the antibiotic(s). Antibodies are added to each cell-antibiotic culture at appropriate dilution and cell growth (e.g. by $OD_{600}$ values) is measured (for instance, every 5 mins for 12 hours in a 96-well spectrophotometer).

EXAMPLE 6

Potassium Channel KcsA

Potassium channel KcsA is related to the P-region and transmembrane helices (S5 and S6) of eukaroytic voltage-gated $K^+$ channel families. KcsA is the first discovered bacterial protein functioning as a $K^+$ channel (Schrempf H et al., EMBO J. 1995 Nov. 1; 14(21):5 170-8). Hegermann J et al have reported in vivo monitoring of the potassium channel KcsA in *Streptomyces lividans* hyphae using immuno-electron microscopy and energy-filtering transmission electron microscopy with a polyclonal antibody to KcsA in *S. lividans*. (Hegermann J et al (2006) Microbiology 152:2831-2841). Antibody directed against bacterial potassium channel is assessed in combination with antibiotics and determined to target the channel in antibiotic-treated cells, using methods including as described above.

EXAMPLE 7

Surface Factor Promoting Resistance to Oxidative Killing (SOK)

Surface factor promoting resistance to Oxidative Killing (SOK) is an *S. aureus* 67.6 kDa predicted protein that contributes to both resistance to killing by human neutrophils and to oxidative stress. An *S. aureus* sok deletion strain showed dramatically reduced aortic valve vegetation and bacterial cell number in a rabbit endocarditis model (Malachowa N et al. Infect Immun 10/1 1/2010 epub). In this study, the authors described and utilize an antibody to *S. aureus* SOK. Antibody directed against bacterial SOK is assessed in combination with antibiotics and determined to target the channel in antibiotic-treated cells, using methods including as described above.

This invention may be embodied in other forms or carried out in other ways without departing from the spirit or essential characteristics thereof. The present disclosure is therefore to be considered as in all aspects illustrate and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

What is claimed is:

1. A composition comprising one or more gram-positive bacteria cell wall or cell membrane disrupter and one or more gram-positive cell wall or cell membrane target inhibiting agent wherein the composition is capable of disrupting the cell wall such that the cell wall or cell membrane target is rendered exposed or accessible and sensitive to the target inhibiting agent, wherein the cell wall or cell membrane target is inaccessible, relatively insensitive, or less sensitive to the target inhibiting agent in the absence of the cell wall disrupting agent, wherein the composition is therapeutically effective to reduce bacterial cell growth, virulence or infection, and wherein the disrupter alone at the composition concentration is not effective in significantly reducing bacterial cell growth, virulence or infection.

2. The composition of claim 1 wherein the disrupter is selected from the group of antibiotics, anti-microbial peptides, polycationic peptides, cell wall degrading enzymes, and catalytic antibodies.

3. The composition of claim 1 wherein the gram-positive bacteria is selected from *Actinomyces, Bacillus, Listeria, Lactococcus, Staphylococcus, Streptococcus, Enterococcus, Mycobacterium, Corynebacterium*, and *Clostridium*.

4. The composition of claim 1 wherein the cell wall or cell membrane target is sortase.

5. The composition of claim 1 wherein the target inhibiting agent is selected from an antibody or antigen binding fragment thereof, a ligand, a bioactive peptide and an enzyme.

6. The composition of claim 1 wherein the gram-positive bacteria is antibiotic resistant.

7. The composition of claim 6 wherein the gram-positive bacteria is antibiotic resistant *Staphylococcus*.

8. The composition of claim 1 wherein the disrupter is an antibiotic that inhibits cell wall synthesis or cell membrane function.

9. The composition of claim 1 wherein the cell wall disrupting agent is an antibiotic and is selected from a glycopeptide, penicillin, cephalosporin, polypeptide/lipopeptide, or carbapanem antibiotic.

10. The composition of claim 1 wherein the cell wall disrupting agent is an antibiotic and is a beta-lactam antibiotic.

11. The composition of claim 1 wherein the cell wall disrupting agent is a cell wall degrading enzyme.

12. The composition of claim 1 wherein the cell wall or cell membrane target is a penicillin binding protein.

13. The composition of claim 1 wherein the target inhibiting agent is a cell wall or cell membrane target inhibiting antibody or antigen binding fragment thereof.

14. The composition of claim 1 wherein the composition is a pharmaceutical composition further comprising a suitable vehicle, carrier, or diluent.

15. The composition of claim 1 wherein the target inhibiting agent is a cell membrane target antibody and the disrupter is an antibiotic in a sub-MIC dose.

* * * * *